US009359303B2

(12) United States Patent
Nichols et al.

(10) Patent No.: US 9,359,303 B2
(45) Date of Patent: Jun. 7, 2016

(54) OCTAHYDROBENZOISOQUINOLINE MODULATORS OF DOPAMINE RECEPTORS AND USES THEREFOR

(75) Inventors: David E. Nichols, West Lafayette, IN (US); Val J. Watts, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 377 days.

(21) Appl. No.: 13/265,454

(22) PCT Filed: Apr. 21, 2010

(86) PCT No.: PCT/US2010/031916
§ 371 (c)(1),
(2), (4) Date: Oct. 20, 2011

(87) PCT Pub. No.: WO2010/124005
PCT Pub. Date: Oct. 28, 2010

(65) Prior Publication Data
US 2012/0041018 A1    Feb. 16, 2012

Related U.S. Application Data

(60) Provisional application No. 61/171,273, filed on Apr. 21, 2009.

(51) Int. Cl.
*C07D 471/04* (2006.01)
*C07D 221/10* (2006.01)
*A61K 31/437* (2006.01)

(52) U.S. Cl.
CPC ............ *C07D 221/10* (2013.01); *A61K 31/437* (2013.01); *C07D 471/04* (2013.01)

(58) Field of Classification Search
CPC .......................... C07D 471/04; A61K 31/437
USPC ............................................. 546/79; 514/290
See application file for complete search history.

(56) References Cited

U.S. PATENT DOCUMENTS

| | | | |
|---|---|---|---|
| 3,912,740 A | 10/1975 | Zee-Cheng et al. | |
| 3,939,165 A | 2/1976 | Schwan | |
| 4,346,090 A | 8/1982 | Humber et al. | |
| 4,737,503 A | 4/1988 | Sakamoto et al. | |
| 5,047,536 A | 9/1991 | Nichols | |
| 5,266,702 A | 11/1993 | Bhaskaran et al. | |
| 5,409,929 A | 4/1995 | Ciganek | |
| 5,420,134 A | 5/1995 | Nichols et al. | |
| 5,597,832 A | 1/1997 | Michaelides et al. | |
| 5,621,133 A * | 4/1997 | DeNinno et al. ............. | 558/286 |
| 5,627,165 A | 5/1997 | Glazier | |
| 5,635,506 A | 6/1997 | Alberts et al. | |
| 5,681,947 A | 10/1997 | Bergstrom et al. | |
| 5,744,476 A | 4/1998 | Locke et al. | |
| 5,959,110 A | 9/1999 | Nichols et al. | |
| 6,194,423 B1 | 2/2001 | Nichols et al. | |
| 6,326,377 B1 | 12/2001 | Lavielle et al. | |
| 6,413,977 B1 | 7/2002 | Nichols et al. | |
| 6,733,797 B1 | 5/2004 | Summers | |
| 6,916,823 B2 | 7/2005 | Mailman et al. | |
| 6,916,832 B2 | 7/2005 | Nichols et al. | |
| 7,220,754 B2 | 5/2007 | Dijkstra et al. | |
| 2005/0232870 A1 | 10/2005 | Mailman et al. | |
| 2006/0264428 A1 | 11/2006 | Takahashi et al. | |
| 2007/0088022 A1 | 4/2007 | Feigelson | |
| 2007/0254906 A1 | 11/2007 | Fernandes et al. | |
| 2009/0030025 A1 | 1/2009 | Nichols et al. | |

FOREIGN PATENT DOCUMENTS

| | | |
|---|---|---|
| DE | 25 29 580 A1 | 2/1976 |
| EP | 0461353 | 12/1991 |
| EP | 0747378 | 12/1996 |
| GB | 2105 323 A | 6/1982 |
| JP | 3-128356 | 5/1991 |
| JP | 4-235167 | 8/1992 |
| WO | WO 90/15056 | 12/1990 |
| WO | WO 92/04356 | 3/1992 |
| WO | WO 96/38435 | 12/1996 |
| WO | WO9638435 | 12/1996 |
| WO | WO99/11649 | 3/1999 |
| WO | WO 2005/062894 | 7/2005 |

OTHER PUBLICATIONS

Cannon, Joseph G., et al. "Congeners of the .alpha. conformer of dopamine derived from octahydrobenz[h]isoquinoline," Journal of Medicinal Chemistry, vol. 23, No. 5, 1980, pp. 502-505.
Ciganek, Engelbert, "The Intramolecular Diels-Alder Reaction," Organic Reactions, 32, no pp given, (1984), Abstract—Chemical Abstracts Service, AN 2008:1383608, 3 pages.
Oppolzer, Wolfgang, "Steric Control of Intramolecular Ortho-Quinodimethanecycloadditions," Tetrahedron letters, No. 12, 1974, pp. 1001-1004.
Archer et al., Pharmacol. Biochem. Behav. 31:357-364, 1988.
Arnsten et al., Dopamine D1 receptor mechanisms in the cognitive performance of young adult and aged monkeys ,Psychopharmacol. 116:143-151, 1994.
Asin et al. "The Selective Dopamine D1 Receptor Agonist A-86929 Maintains Efficacy with Repeated Treatment in Rodent and Primate Models of Parkinson's Disease," J. Pharm. and Exper. Ther. 281: 454-459 (1997).
Berge, S.M., Bighley, L.D., and Monkhouse, D.C., "Pharmaceutical Salts," J. Pharm. Sci., vol. 66, No. 1, 1977, pp. 1-19.
Bradley, K.C., Mullins, A.J., Meisel, R.L., and Watts, V.J., "Sexual Experience Alters D1 Receptor-Mediated Cyclic AMP Production in the Nucleus Accumbens of Female Syrian Hamsters," Synapse, vol. 53, No. 1, 2004, pp. 20-27.

(Continued)

*Primary Examiner* — Rita Desai
(74) *Attorney, Agent, or Firm* — Mark S. Cohen; Pearl Cohen Zedek Latzer Baratz LLP

(57) ABSTRACT

Octahydrobenzoisoquinoline modulators of dopamine receptors are described herein. Methods for using octahydrobenzoisoquinoline modulators of dopamine receptors in the treatment of dopamine dysfunction are also described herein.

4 Claims, No Drawings

(56) References Cited

OTHER PUBLICATIONS

Brewster, W.K., Nichols, D.E., Riggs, R.M., Mottola, D.M., Lovenberg, T.W., Lewis, M.H., and Mailman, R.B., "Trans-10,11-Dihydroxy-5,6,6a,7,8,12b-Hexahydrobenzo[a]phenanthridine: a Highly Potent Selective Dopamine D1 Full Agonist," J. Med. Chem., vol. 33, 1990, pp. 1756-1764.
Castro et al. "Increased or Decreased Locomotor Response in Rats Following Repeated Administration of Apomorphine Depends on Dosage Interval," Psychopharm. 85: 333-339 (1985).
Chemical Abstracts CA111: 187294.
Chemical Abstracts CA112: 235152.
Chemical Abstracts CA115: 256024.
Chemical Abstracts CA115: 717.
Chemical Abstracts CA115: 85324.
Chemical Abstracts CA116: 51351.
Chemical Abstracts CA117: 26359.
Chemical Abstracts CA83: 141745.
Colombo et al., "Allocentric spatial and tactile memory impairments in rats with dorsal caudate lesions are affected by preoperative behavioral training.," Behav. Neurosci. 103:1242-1250, 1989.
Cueva, J.P., Giorgioni, G., Grubbs, R.A., Chemel, B.R., Watts, V.J., and Nichols, D.E., "Trans-2,3-Dihydroxy-6a,7,8,12b-Tetrahydro-6H-Chromeno[3,4-c]isoquinoline: Synthesis, Resolution, and Preliminary Pharmacological Characterization of a New Dopamine D1 Receptor Full Agonist," J. Med. Chem., vol. 49, 2006. pp. 6848-6857.
Dorland's Illustrated Medical Dictionary 26.sup.th Ed Saunders, Philadelphia, pp. 401 and 856, 1981.
Elmore & King, "Synthesis of 8-lsopropylpodocarpane-6,7-Diol (6-Hydroxytotarol) and of 7,8-Dimethoxypodocarpane," J. Chem. Soc., p. 4425 (1961).
Gancher et al. "Time Course of Tolerance to Apomorphine in Parkinsonism," Clin. Pharmacol. Ther. 52: 504-510 (1992).
Gay, E.A., Urban, J.D., Nichols, D.E., Oxford, G.S., and Mailman, R.B., "Functional Selectivity of $D_2$ Receptor Ligands in a Chinese Hamster Ovary $hD_{2L}$ Cell Line: Evidence for Induction of Ligand-Specific Receptor States," Molecular Pharmacology, vol. 66, No. 1, 2004, pp. 97-105.
Ghosh et al, "8,9-Dihydroxy-2,3,7,11b-tetrahydro-1H-naph[1,2,3-de]isoquinoline: A Potent Full Dopamine D1 Agonist Containing a Rigid β-Phenyldopamine Pharmacophore,"J. Med. Chem., vol. 39 pp. 549-555 (1996).
Gilmore, J.H., Watts, V.J., Lawler, C.P., Noll, E.P., Nichols, D.E., and Mailman, R.B., "'Full' Dopamine D1 Agonists in Human Caudate: Biochemical Properties and Therapeutic Implications," Neuropharmacology, vol. 34, No. 5, 1995, pp. 481-488.
Gordon N. Walker, Hypotensive Methoxyisoquinolines, JACS, vol. 76, pp. 3999-4003 (1954).
Goulet, et al. "Dyskinesias and Tolerance Induced by Chronic Treatment with a D1 Agonist Administered in Pulsatile or Continuous Mode Do Not Correlate with Changes of Putaminal D1 Recptors in Drug-Naive MPTP Monkeys," Brain Res. 719: 129-137 (1996).
Grandas et al. "Time Interval Between Repeated Injections Conditions the Duration of Motor Improvement by Apomorphine in Parkinson's Disease," Neurology 42: 1287-1290 (1992).
Grondin et al. "Potential Therapeutic Use of the Selective Dopamine D1 Receptor Agonist, A-86929: An Acute Study in Parkinsonian Levodopa-Primed Monkeys," Neurology 49: 421-426 (1997).
Grubbs, Russell A., Synthesis of Novel Dopaminergic Ligands: A Bioisosteric Approach (Aug. 2000) (unpublished Ph.D. Thesis, Purdue University), microformed on UMI Microform 3018202 (2001) (Bell & Howell Information and Learning Company).
Guide for the Care and Use of Experimental Animals published by the National Institutes of Health (Pub. 85-23, 1985).
Gulwadi, et al. "Dinapsoline: Characterization of a D1 Dopamine Receptor Agonist in a Rat Model of Parkinson's Disease," J. Pharm. and Exper. Ther. 296: 338-344 (2001).
International Search Report for International Application No. PCT/US2007/062481, Jun. 6, 2008, 17 pages.
Johnson, D.E., Ochieng, J., and Evans, S.L., "The Growth Inhibitory Properties of a Dopamine Agonist (SKF 38393) on MCF-7 Cells," Anti-Cancer Drugs, vol. 6, No. 3, 1995, pp. 471-474.
Kirby & Polgar, Physiol. Psychol. 2:301-306, 1974.
Knoerzer, T.A., Nichols, D.E., Brewster, W.K., Watts, V.J., Mottola, D., and Mailman, R.B., "Dopaminergic Benzo[a]phenanthridines: resolution and pharmacological evaluation of the Enantiomers of Dihydrexidine, the Full Efficacy D1 Dopamine Receptor Agonist," J. Med. Chem., vol. 37, No. 15, 1994, pp. 2453-2460.
Kohli, J. D., Dopamine Receptor Agonists and Antagonists, Proc. West. Pharmacol. Soc., vol. 33, pp. 21-27 (1990).
Laus G., D. Tourwe, G. Van Binst, Benzo-and Indoloquinolizidine Derivatives XIX. The Synthesis and Pharmacological Activity of Some Quinolizidine Derivatives, Analogues of Butaclamol, Heterocycles, vol. 22, No. 2, pp. 311-331 (1984).
Lin et al. "Persistent Activation of the Dopamine D1 Receptor Contributes to Prolonged Receptor Desensitization: Studies with A-77636," J. Pharm. and Exper. Ther. 276: 1022-1029 (1996).
Menon, M. K., W. G. Clark, J. G. Cannon, Comparison of the Dopaminergic Effects of N-substituted Aporphines, J. Pharm. Pharmac., Communications, vol. 28, pp. 778-781 (1976).
Michaelides, M.R., Hong, Y., DiDomenico, Jr., S., Bayburt, E.K., Asin, K.E., Britton, D.R., Lin, C.W., and Shiosaki, K., "Substituted Hexahydrobenzo[f]thieno[c]quinolines as Dopamine D1-Selective Agonists: Synthesis and Biological Evaulation in Vitro and in Vivo," J. Med. Chem., vol. 40, 1997, pp. 1585-1599.
Neill et al., Pharmacol. Biochem. Behav. 2:97-103 (1974).
Nichols & Dyer, "Lipophilicity and serotonin agonist activity in a series of 4-substituted mescaline analogues," J. Med. Chem., 20:299-301 (1977).
Nichols et al "Development of Potentially Selective Dopamine Agonists", Experimental Methods p. 29. (Jun. 1990) NIH Grant paper.
Oka et al., "Synthesis of Conformationally Rigid Catecholamine Derivatives," Chem. Pharm. Bull., 25:632-639 (1977).
Packard & White, "Dissociation of hippocampus and caudate nucleus memory systems by posttraining intracerebral injection of dopamine agonists."Behav. Neurosci. 105:295-306. 1991.
Packard and White, "Lesions of the caudate nucleus selectively impair," Behay. Neural. Biol. 53:39-50, 1990.
Packard et al., "Differential effects of fornix and caudate nucleus lesions on two radial maze tasks: evidence for multiple memory systems," J. Neurosci. 9:1465-72, 1989.
Pathak et al., Enzymic protecting group techniques in organic synthesis, Stereosel. Biocatal. 775-797 (2000).
Polgar et al., "Is the striatum involved in passive-avoidance behavior? A commentary.," Physiol. Psychol. 9:354-358. 1981.
PCT International Search Report; Application No. PCT/US2010/031916, Jun. 18, 2010, 2 pages.
Pitfield, S.E., Bryant, I., Penington, D.J., Park, G., and Riese II, D.J., "Phosphorylation of ErbB4 on Tyrosine 1056 is Critical for ErbB4 Coupling to Inhibition of Colony Formation by Human Mammary Cell Lines," Oncology Research Featuring Preclinical and Clinical Cancer Therapeutics, vol. 16, No. 4, 2006, pp. 179-193.
Riggs, et al., "Specific Dopamine D-1 and DA.sub.1 Properties of 4-(Mono- and -dihydroxyphenyl)-1,2,3,4-tetrahydroisoquinoline and Its Tetrahydrothieno[2,3-c ]pyridine Analogues," 1987, J. Med. Chem., vol. 30, No. 8, pp. 1454-1458.
Robert Mack Riggs, Studies Directed Toward the Design of Specific Dopamine D-1/DA-1 Agonists and Antagonists, A Thesis Submitted to the Faculty of Purdue University, 1986.
Ryman et al. "Tolerance induced by infusion of dopamine D1 feceptor full agonists in dopamine-denervated rats," Society for Neuroscience Abstract, 1999. vol. 25, No. 1-2 p. 60. ISSN: 0190-5295.
Sami, et al., "2-substituted 1,2-dihydro-3H-dibenz [de,h] isoquinoline-1,3-diones. A New Class of Antitumor Agent." Mar. 19, 1993, J. Med. Chem., vol. 36, No. 6, pp. 765-770.
Sami, et al., "6- and 7-Substituted 2-[2'-(Dimethylamino)ethyl]-1,2-dihydro-3H-dibenz [de,h] isoquinoline-1 ,3-diones: Synthesis, Nucleophilic Displacements, Antitumor Activity, and Quantitative Structure-Activity Relationships." Apr. 12, 1996, J. Med. Chem., vol. 39, No. 8, pp. 1609-1618.

(56) References Cited

OTHER PUBLICATIONS

Sami, et al., "Amino-substituted 2-[2'-(dimethylamino)ethyl]-1,2-dihydro-3H-debenz[de,h] isoquinoline-1,3-diones. Synthesis, Antitumor Activity, and Quantitative Structure-Activity Relationship," Mar. 17, 1995, J. Med. Chem.,vol. 38, No. 6, pp. 983-993.

Sanji Hagishita, Motoo Shiro, Kaoru Kuriyama, Synthesis and C.d. Spectra of 6,6a,7,11b-Tetrahydro-5H-indeno[2,1-c]-isoquinoline Derivatives, J. Chem. Soc. Perkin Trans. 1, vol. 8, pp. 1655-1669 (1984).

Taber et al. "Characterization of the D1 Agonist Dinapsoline in the Unilateral 6-OHDA Lesioned Rat," Society for Neuroscience Abstr. 26: Abstr. 809.3 (2000).

Watts, V.J., Lawler, C.P., Gonzales, A.J., Zhou, Q.Y., Civelli, O., Nichols, D.E., and Mailman, R.B., "Spare Receptors and Intrinsic Activity: Studies with D1 Dopamine Receptor Agonists," Synapse, vol. 21, No. 2, 1995, pp. 177-187.

Wei, Chung-Chen, Sidney Teitel, Synthesis of a Benzo[a]Phenanthridine Isomeric With Apomorphine, Heterocycles, vol. 8, pp. 97-102 (1977).

Wishaw & Dunnett, Behav. Brain. Res. 18:11-29, 1985.

Wishaw et al., "Impairments in the acquisition, retention and selection of spatial navigation strategies after medial caudate-putamen lesions in rats,"Behav. Brain. Res. 24:125-138, 1987.

* cited by examiner

OCTAHYDROBENZOISOQUINOLINE MODULATORS OF DOPAMINE RECEPTORS AND USES THEREFOR

CROSS REFERENCE TO RELATED APPLICATIONS

This application is a U.S. national counterpart application of international application serial No. PCT/US2010/031916 filed Apr. 21, 2010, which claims priority to U.S. Provisional Patent Application No. 61/171,273 filed Apr. 21, 2009. The entire disclosures of PCT/US2010/031916 and U.S. Ser. No. 61/171,273 are hereby incorporated by reference.

GOVERNMENT RIGHTS

This invention was made with government support under grant numbers MH42705 and MH60397 awarded by the National Institutes of Health. The government has certain rights in the invention.

TECHNICAL FIELD

The invention described herein pertains to modulators, including agonists and antagonists of dopamine receptors. In particular, the invention described herein pertains to octahydrobenzoisoquinoline modulators of dopamine receptors.

BACKGROUND AND SUMMARY OF THE INVENTION

Dopamine (DA) is a neurotransmitter that is important in locomotor control, reward circuitry, cognitive function, prolactin release and a variety of other key physiological functions. Dopaminergic dysfunctions have been implicated in Parkinson's disease, schizophrenia, addiction, attention deficit hyperactivity disorder (ADHD), and certain sexual dysfunctions.

It is has been reported that there are at least two pharmacological subtypes of dopamine receptors (the $D_1$ and $D_2$ receptor subtypes), each consisting of several molecular forms. $D_1$ receptors preferentially recognize the phenyltetrahydrobenzazepines and generally lead to stimulation of the enzyme adenylate cyclase, whereas $D_2$ receptors recognize the butyrophenones and benzamides and often are coupled negatively to adenylate cyclase, or are not coupled at all to this enzyme. It has also been reported that at least five dopamine receptor genes encode the $D_1$, $D_2$, $D_3$, $D_4$ and $D_5$ receptor isoforms or subtypes. The traditional classification of dopamine receptor subtypes, however, remains useful with the $D_1$-like class comprising the $D_1$ ($D_{1A}$) and the $D_5$ ($D_{1B}$) receptor subtypes, whereas the $D_2$-like class consists of the $D_2$, $D_3$ and $D_4$ receptor subtypes. Agonist stimulation of dopamine $D_1$ receptors is believed to activate adenylate cyclase to form cyclic AMP (cAMP), which in turn is followed by the phosphorylation of intracellular proteins. Agonist stimulation of $D_2$ dopamine receptors is believed to lead to decreased cAMP formation. Agonists at both subclasses of receptors are clinically useful. In addition, antagonists at both subclasses of receptors are clinically useful.

Dopamine receptor agonists are of therapeutic interest for a variety of reasons. For example, it has been hypothesized that excessive stimulation of $D_2$ dopamine receptor subtypes may be linked to schizophrenia. Additionally, it is generally recognized that either excessive or insufficient dopaminergic activity in the central nervous system can cause hypertension, narcolepsy, and other behavioral, neurological, physiological, and movement disorders, including Parkinson's disease. For example, schizophrenia is among the most common and the most debilitating of psychiatric diseases. Current estimates suggest a prevalence of schizophrenia at between 0.5 and 1% of the population.

Patients with schizophrenia and other neurological and psychiatric disorders, such as psychosis, bipolar disorder, anxiety states, and depression in combination with psychotic episodes, can have both "positive" symptoms, including delusions, hallucinations, impaired cognitive function, and agitation, as well as "negative" symptoms, including emotional unresponsiveness, impaired memory, and impaired cognitive function. Patients with these psychotic signs and symptoms can be treated with drugs that fall into the general classes of typical antipsychotic drugs and atypical antipsychotic drugs. The typical antipsychotic agents include phenothiazines, butyrophenones, and other non-phenothiazines such as loxapine and molindone. The atypical antipsychotic agents include the clozapine-like drugs, such as clozapine, olanzepine, quetiapine, ziprasidone, and the like, as well as several others, including risperidone, aripiprazole, and amisulpiride, among others. Whereas both of these typical and atypical antipsychotic agents are useful for treating the positive symptoms of the neurological disorders described herein, patients may not find total relief from the negative symptoms that may accompany these antipsychotic agents. In addition, recent studies suggest that the current antipsychotic therapy for treating positive symptoms of schizophrenia may in some cases exacerbate or facilitate the onset of such negative symptoms.

Dopamine agonists have also been developed to treat Parkinson's disease in an attempt to avoid some of the limitations of levodopa therapy, because levodopa therapy is not always a successful treatment, for example in certain late-stage disorders. In addition, by acting directly on postsynaptic dopamine receptors, selective dopamine agonists bypass the degenerating presynaptic neurons. Furthermore, these drugs do not rely on the same enzymatic conversion for activity required for levodopa, avoiding issues associated with declining levels of striatal dopa decarboxylase. In addition, agonists have the potential for longer half-lives than levodopa, and can also be designed to interact specifically with predetermined subpopulations of dopamine receptors.

However, it has been shown that administering a $D_2$ receptor antagonist down regulates $D_1$ receptors. Such down regulation was shown to have the overall effect of causing or increasing memory and cognition complications. Down regulation of $D_1$ and/or $D_5$ receptor mRNAs has been observed in the prefrontal and temporal cortices but not in the neostriatum of nonhuman primates after chronic treatment with certain antipsychotic medications.

In addition, numerous reports have been made that full $D_1$ agonists may cause $D_1$ receptor desensitization and even down regulation of dopamine $D_1$ receptor expression. Partial $D_1$ agonists may cause desensitization but generally do not cause down regulation of receptor expression. In addition, it has also been shown that short-term administration of a $D_1$ receptor agonist following the onset of memory or cognition complications arising from administering a $D_2$ receptor antagonist, alleviated the symptoms of such memory or cognition complications.

Accordingly, a need still exists for additional agonists and antagonists of dopamine receptors. In addition, full agonists at dopamine receptors are also needed. In addition, agonists and antagonists that show dopamine receptor subtype selectivity are also needed.

It has been discovered that compounds described herein are modulators of dopamine receptors, including agonists and antagonists of dopamine receptors. In addition, compounds described herein are full agonists at dopamine receptors. In addition, compounds described herein are agonists and antagonists that show dopamine receptor subtype selectivity are also needed. In one embodiment, compounds are described herein that are agonists selective for $D_1$ and/or $D_1$-like dopamine receptors In another embodiment, octahydrobenzo[h]isoquinoline compounds are described herein, such as compounds of the following formula

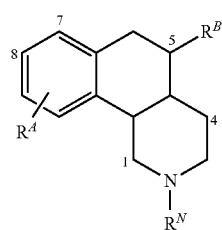

including pharmaceutically acceptable salts thereof, wherein:

$R^A$ is hydrogen; or $R^A$ represents 1-4 substituents selected from the group consisting of halo, hydroxy, and amino, and derivatives thereof, and alkyl and heteroalkyl, each of which is optionally substituted; where two adjacent substituents are optionally taken together with the attached carbons to form an optionally substituted heterocycle;

$R^B$ is hydrogen; or $R^B$ is alkyl, heteroalkyl, cycloalkyl, cycloheteroalkyl, aryl, heteroaryl, arylalkyl, or heteroarylalkyl, each of which is optionally substituted; and $R^N$ is hydrogen or an amino prodrug group; or $R^N$ is alkyl, heteroalkyl, cycloalkyl, cycloheteroalkyl, aryl, heteroaryl, arylalkyl, or heteroarylalkyl, each of which is optionally substituted.

In another embodiment, compositions are described herein for treating neurological, psychotic, and/or psychiatric disorders. The compositions include therapeutic amounts of one or more compounds described herein, which may be administered to a patient or subject in need of relief from or suffering from the neurological, psychotic, and/or psychiatric disorder. The compositions described herein may include pharmaceutically active carriers, diluents, and/or excipients.

In another embodiment, methods are described herein for treating neurological, psychotic, and/or psychiatric disorders. The methods include the step of administering therapeutic amounts of one or more compounds described herein to a patient or subject in need of relief from or suffering from the neurological, psychotic, and/or psychiatric disorder.

In another embodiment, uses are described herein for manufacturing medicaments for treating neurological, psychotic, and/or psychiatric disorders. The medicaments include therapeutic amounts of one or more compounds described herein, which may be used to treat to a patient or subject in need of relief from or suffering from the neurological, psychotic, and/or psychiatric disorder.

DETAILED DESCRIPTION

Optionally substituted octahydrobenzoisoquinoline compounds of formula (I)

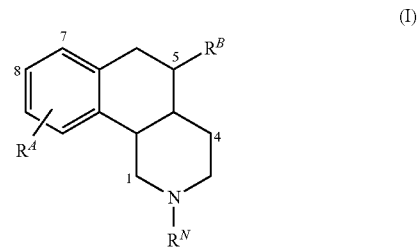

including the corresponding pharmaceutically acceptable salts, hydrates, and/or solvates thereof, are described herein; wherein:

$R^A$ is hydrogen; or $R^A$ represents 1-4 substituents selected from the group consisting of halo, hydroxy, and amino, and derivatives thereof, and alkyl and heteroalkyl, each of which is optionally substituted; where two adjacent substituents are optionally taken together with the attached carbons to form an optionally substituted heterocycle;

$R^B$ is hydrogen; or $R^B$ is alkyl, heteroalkyl, cycloalkyl, cycloheteroalkyl, aryl, heteroaryl, arylalkyl, or heteroarylalkyl, each of which is optionally substituted; and $R^N$ is hydrogen or an amino prodrug group; or $R^N$ is alkyl, heteroalkyl, cycloalkyl, cycloheteroalkyl, aryl, heteroaryl, arylalkyl, or heteroarylalkyl, each of which is optionally substituted.

In another embodiment, $R^A$ is hydrogen or 1-4 substituents selected from the group consisting of fluoro, chloro, bromo, iodo or optionally substituted $C_1$-$C_4$ alkyl, optionally substituted heteroalkyl, amino (including $NH_2$, RNH, $R_2N$ where R can be the same or different), or a group of the formula —OR wherein R is hydrogen, or alkyl, including $C_1$-$C_4$ alkyl, acyl, arylalkyl, alkanoyl, including $C_1$-$C_4$ alkanoyl, benzoyl, pivaloyl, or an optionally substituted phenyl or phenoxy protecting group, each of which is optionally substituted; or when two adjacent substituents $R^A$ are groups of the formula —OR or —$NR_2$, as defined herein, the groups R can optionally be taken together to form a heterocycle;

$R^B$ is hydrogen, alkyl, heteroalkyl, aryl, heteroaryl, arylalkyl, or heteroarylalkyl, each of which is optionally substituted; and $R^N$ is hydrogen, alkyl, heteroalkyl, aryl, heteroaryl, arylalkyl, or heteroarylalkyl, each of which is optionally substituted.

In another embodiment, $R^A$ represents 1-4 substituents selected from the group consisting of halo, hydroxy, and amino, $C_1$-$C_4$ alkyl, and heteroalkyl, each of which is optionally substituted. In another embodiment, $R^A$ represents 1-4 substituents selected from the group consisting of halo, hydroxy, amino, and derivatives thereof. In another embodiment, $R^A$ represents 1-4 substituents selected from the group consisting of halo, hydroxy, amino, and derivatives thereof, where two adjacent substituents are taken together with the attached carbons to form an optionally substituted heterocycle. In another embodiment, $R^A$ includes at least one hydroxy or a hydroxy derivative. In another embodiment, $R^A$ includes at least one hydroxy or a hydroxy prodrug. In another embodiment, $R^A$ includes C7 hydroxy. In another embodiment, $R^A$ includes C8 hydroxy. In another embodiment, $R^A$ includes C7,C8 dihydroxy. In another embodiment, $R^A$ includes C7 halo. In another embodiment, $R^A$ includes C8 halo. In another embodiment, substituted hydroxy is selected from the group consisting of alkoxy, including $C_1$-$C_4$ alkoxy, arylalkoxy, and acyloxy, each of which is optionally substituted, including $C_1$-$C_4$ alkanoyl, pivaloyl, benzoyl, and the like, and phenoxy protecting groups. In another embodiment, $R^A$ is 7,8-dihydroxy or derivatives thereof. In another embodiment, $R^A$ is 7,8-methylene dioxy or 7,8-ethylenedioxy.

In another embodiment, when two adjacent substituents $R^A$ are groups of the formula —OR or —$NR_2$, as defined herein, the groups R can optionally be taken together to form a —$CH_2$— or —$(CH_2)_2$— group.

In another embodiment, $R^B$ is alkyl, heteroalkyl, cycloalkyl, cycloheteroalkyl, aryl, heteroaryl, arylalkyl, or heteroarylalkyl, each of which is optionally substituted. In another embodiment, $R^B$ is cycloalkyl, cycloheteroalkyl, aryl, or heteroaryl, each of which is optionally substituted. In another embodiment, $R^B$ is adamantyl. In another embodiment, $R^B$ is aryl or heteroaryl, each of which is optionally substituted. In another embodiment, $R^B$ is phenyl or monocyclic heteroaryl, each of which is optionally substituted. In another embodiment, $R^B$ is substituted phenyl or substituted monocyclic heteroaryl, where the substituents are selected from the group consisting of hydroxy, amino, carboxylic acid, and derivatives thereof.

In another embodiment, $R^N$ is hydrogen or an amino prodrug.

In another illustrative embodiment, the octahydrobenzoisoquinoline compound of Formula (I) includes compounds wherein $R^A$ includes C7-C8 dihalo. In another illustrative embodiment, the octahydrobenzoisoquinoline compound of Formula (I) includes compounds wherein $R^A$ includes C8 halo. In yet another illustrative embodiment, the octahydrobenzoisoquinoline compound of Formula (I) includes compounds wherein $R^A$ includes C7 halo.

In another illustrative embodiment, the octahydrobenzoisoquinoline compound of Formula (I) includes compounds wherein $R^B$ is hydrogen, or optionally substituted alkyl, heteroalkyl, aryl, heteroaryl, arylalkyl, or heteroarylalkyl, and the like.

It is to be understood that each of the foregoing embodiments may be combined without limitation in chemically relevant ways. For example, in an illustrative alternative embodiment, $R^A$ represents 1-4 substituents selected from the group consisting of halo, hydroxy, amino, and derivatives thereof; $R^B$ is aryl or heteroaryl, each of which is optionally substituted; and $R^N$ is hydrogen or an amino prodrug. In another illustrative alternative embodiment, $R^A$ includes C7,C8 dihydroxy; $R^B$ is cycloalkyl, cycloheteroalkyl, aryl, or heteroaryl, each of which is optionally substituted; and $R^N$ is hydrogen or an amino prodrug. Additional combinations of each of the foregoing embodiments are implicitly described herein as further embodiments.

In another illustrative embodiment, the octahydrobenzoisoquinoline compound of Formula (I) includes each of the possible stereoisomers (e.g., enantiomers and/or diastereomers) in optically pure form, or in various mixtures of enantiomers or diastereomers. In addition, the various mixtures of these stereoisomers also include racemic mixtures that are formed from one pair of enantiomers. Exemplary of the optically pure compounds or mixtures of compounds of Formula (I) are compounds or mixtures of compounds wherein the chiral centers have the following relative stereochemistry:

In another embodiment, the chiral carbons in each of the foregoing embodiments have the following relative stereochemistry

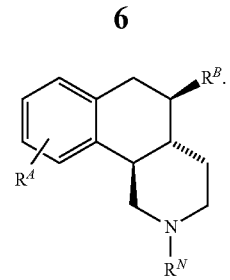

In another embodiment, the chiral carbons in each of the foregoing embodiments have the following absolute stereochemistry

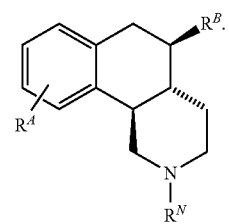

In another embodiment, pharmaceutical compositions comprising one or more compounds described herein, and one or more pharmaceutically acceptable carriers, excipients, or diluents therefore are described. The compositions include a therapeutically effective amount of the one or more compounds for treating a neurological, psychotic, and/or psychiatric disorder.

In another embodiment, methods for treating a patient in need of relief from a disease arising from dopamine dysfunction are described herein. The methods include the step of administering to the patient a therapeutically effective amount of one or more compounds described herein, or a pharmaceutical composition thereof, wherein such pharmaceutical compositions include one or more of the compounds, and one or more pharmaceutically acceptable carriers, excipients, or diluents therefor. The methods include administering a therapeutically effective amount of the one or more compounds for treating a neurological, psychotic, and/or psychiatric disorder.

As used herein, the term "$D_1$-like receptor" refers to each and every $D_1$ and $D_1$-like receptor, alone or in various combinations, including the $D_1$ and $D_5$ receptors in humans, the $D_{1A}$ and $D_{1B}$ receptors found in rats, and other $D_1$-like receptors.

The compounds, compositions, and methods described herein are useful for administration and/or co-administration of dopamine receptor-binding compounds including partial and/or full dopamine $D_1$ receptor agonists and antagonists. The dopamine $D_1$ receptor agonists may have biological activities ranging from compounds with selective $D_1$ receptor agonist activity to compounds with potent activities affecting both $D_1$ and $D_2$ dopamine receptors and various subtypes thereof. In accordance with the methods and compositions described herein, an effective amount of a partial and/or full $D_1$ receptor agonist or antagonist may be administered, either alone or co-administered with another partial and/or full $D_1$ receptor agonist or antagonist, and either in the same or in a different composition or compositions, to a patient having a neurological disorder to reduce the symptoms of the neurological disorder (e.g., to reduce both the positive and the negative symptoms of neurological disorders such as schizophrenia). Likewise, in accordance with the methods and compositions described herein, an effective amount of a partial and/or full $D_1$ receptor agonist can be co-administered to a patient having a neurological disorder along with an effective amount of a $D_2$ receptor antagonist to reduce the symptoms of the neurological disorder, either in the same or in a different composition or compositions.

In one embodiment, the compounds described herein are selective for dopamine $D_1$-like receptors, such as the $D_1$ ($D_{1A}$) and the $D_5$ ($D_{1B}$) receptors. In another embodiment, the compounds described herein are selective for dopamine $D_1$ receptors.

The compounds useful in the methods and compositions described herein for treating neurological, psychotic, and/or psychiatric disorders include partial and/or full dopamine $D_1$ receptor agonists and/or antagonists. The partial and/or full $D_1$ receptor agonists and/or antagonists may be administered alone or co-administered either contemporaneously or simultaneously. In accordance with the methods and compositions described herein, an effective amount of a partial and/or full $D_1$ receptor agonist and/or antagonist can be administered either alone or co-administered to a patient having a neurological disorder to reduce the symptoms of the neurological, psychotic, and/or psychiatric disorder. The partial and/or full $D_1$ receptor agonist or antagonist can be administered to the patient having the neurological disorder either alone or co-administered in the same or in a different composition or compositions. It is appreciated that simultaneous co-administration is facilitated by a unit or unitary dosage form that includes both the partial and/or full $D_1$ receptor agonists and antagonists. It is also understood that the compounds described herein may exhibit functional selectivity at one or more dopamine receptors.

In another embodiment, the methods include the administration of a compound described herein that is a dopamine receptor agonist. In another embodiment, the methods include the administration of a compound described herein that is a $D_1$ dopamine receptor agonist. In another embodiment, the methods include the administration of a compound described herein that is a selective $D_1$ dopamine receptor agonist.

In another embodiment, the methods include the administration of a compound described herein that is a dopamine receptor partial agonist. In another embodiment, the methods include the administration of a compound described herein that is a dopamine receptor full agonist. In another embodiment, the methods include the administration of a compound described herein that is a dopamine receptor partial agonist. In another embodiment, the methods include the administration of a compound described herein that is a dopamine receptor antagonist. In another embodiment, the methods include the administration of a compound described herein that is a $D_1$ dopamine receptor antagonist. In another embodiment, the methods include the administration of a compound described herein that is a selective $D_1$ dopamine receptor antagonist.

Illustrative selectivity is a compound showing an affinity ratio for the $D_1$ receptor to the $D_2$ receptor and/or $D_1$-like receptors to $D_2$-like receptors of at least about 2, at least about 5, at least about 10, at least about 20, at least about 25, or at least about 50.

In another embodiment, disclosed herein is a method for treating a patient in need of relief from a disease arising from dopamine dysfunction, the method comprising the step of administering to the patient a therapeutically effective amount of a mixture of compounds of Formula I, or a pharmaceutical composition thereof, and one or more pharmaceutically acceptable carriers, excipients, or diluents therefor. In one illustrative example, the mixture of compounds may comprise two or more dopamine receptor agonists. In another illustrative example, the mixture of compounds may comprise two or more dopamine receptor antagonists. In yet another illustrative example, the mixture of compounds may comprise one or more dopamine receptor agonists and one or more dopamine receptor antagonists. In yet another illustrative example, the dopamine receptor agonist or antagonist is a $D_1$ dopamine receptor agonist or antagonist.

In another embodiment, disclosed herein is a method for treating a patient in need of relief from a disease arising from dopamine dysfunction, the method comprising the step of administering to the patient a therapeutically effective amount of one or more compounds of Formula I, or a pharmaceutical composition thereof, wherein the pharmaceutical composition comprises one or more compounds of Formula I, and one or more pharmaceutically acceptable carriers, excipients, or diluents therefor, and wherein the compound is a dopamine receptor agonist. In an illustrative example, the one or more compounds include a $D_1$ dopamine receptor agonist and/or a $D_1$ dopamine receptor antagonist. In another illustrative example, the $D_1$ dopamine receptor agonist and/or a $D_1$ dopamine receptor antagonist of Formula I is optically active. In yet another illustrative example, the disease arising from dopamine dysfunction includes Parkinson's disease, schizophrenia, a memory disorder, a cognitive disorder, or a movement disorder.

In another embodiment, methods are described herein for treating Parkinson's disease. In another embodiment, methods are described herein for treating schizophrenia. In another embodiment, methods are described herein for treating a memory disorder. In another embodiment, methods are described herein for treating a memory disorder that is drug-induced. In another embodiment, methods are described herein for treating a memory disorder that is age-related. In another embodiment, methods are described herein for treating a working memory deficit in schizophrenia. In another embodiment, methods are described herein for improving working memory in a schizophrenia patient. In another embodiment, methods are described herein for increasing prefrontal cortical blood flow. It is to be understood that increasing prefrontal cortical blood flow may indicate a demand for oxygen and glucose by the prefrontal cortex, and may indirectly demonstrate enhanced cortical function. In another embodiment, methods are described herein for treating a cognitive disorder. In another embodiment, methods are described herein for treating a cognition deficit in schizophrenia. In another embodiment, methods are described herein for improving cognition in a schizophrenia patient. In another embodiment, methods are described herein for treating a movement disorder.

Additional illustrative neurological disorders that can be treated with the methods, compounds, and compositions described herein include such neurological disorders as schizophrenia, schizophreniform disorder, schizoaffective disorders, including those characterized by the occurrence of a depressive episode during the period of illness, bipolar disorder, depression in combination with psychotic episodes, and other disorders that include a psychosis. The types of schizophrenia that may be treated include Paranoid Type Schizophrenia, Disorganized Type Schizophrenia, Catatonic Type Schizophrenia, Undifferentiated Type Schizophrenia, Residual Type Schizophrenia, Schizophreniform Disorder, Schizoaffective Disorder, Schizoaffective Disorder of the Depressive Type, and Major Depressive Disorder with Psychotic Features. Typically, the neurological disorders that can be treated have both "positive" symptoms (e.g., delusions, hallucinations, impaired cognitive function, and agitation) and "negative" symptoms (e.g., emotional unresponsiveness).

It is to be understood that various forms of schizophrenia may be treatable using the methods and compositions described herein. It is also appreciated that psychotic conditions as described herein include schizophrenia, schizophreniform diseases, acute mania, schizoaffective disorders, and depression with psychotic features. The titles given these conditions may represent multiple disease states. Illustratively, the disease state may be referenced by the classification in the Diagnostic and Statistical Manual of Mental Disorders, 4th Edition, published by the American Psychiatric Association (DSM). The DSM code numbers for several disease states include Paranoid Type Schizophrenia 295.30, Disorganized Type Schizophrenia 295.10, Catatonic Type Schizophrenia 295.20, Undifferentiated Type Schizophrenia 295.90, Residual Type Schizophrenia 295.60, Schizophreniform Disorder 295.40, Schizoaffective Disorder 295.70, Schizoaffective Disorder of the Depressive Type and Major Depressive Disorder with Psychotic Features 296.24, 296.34. It is also understood that psychoses are often associated with other diseases and conditions, or caused by such other conditions, including with neurological conditions, endocrine conditions, metabolic conditions, fluid or electrolyte imbalances, hepatic or renal diseases, and autoimmune disorders with central nervous system involvement, and with use or abuse of certain substances, including but not limited to cocaine, methylphenidate, dexmethasone, amphetamine and related substances, cannabis, hallucinogens, inhalants, opioids, phencyclidine, sedatives, hypnotics, and anxiolytics. Psychotic disorders may also occur in association with withdrawal from certain substances. These substances include, but are not limited to, sedatives, hypnotics and anxiolytics. Another disease state treatable with the methods and compositions described herein includes schizotypal personality disorder, a schizophrenia spectrum disorder that is related genetically, phenomenology, and neurobiology, and pharmacologically to chronic schizophrenia, and shares many of the cognitive deficits of schizophrenia, although typically to a lesser degree of severity.

Other disorders that have a psychotic component and a depressive component that can be treated include premenstrual syndrome, anorexia nervosa, substance abuse, head injury, and mental retardation. Additionally, endocrine conditions, metabolic conditions, fluid or electrolyte imbalances, hepatic or renal diseases, and autoimmune disorders with central nervous system involvement which have a psychotic component and a depressive component may be treated with the composition and method described herein.

In another illustrative embodiment, the partial and/or full $D_1$ dopamine receptor agonist can be selective for a dopamine $D_1$ receptor subtype, such as the $D_1$ or $D_5$ receptor subtype in humans, or the $D_{1A}$ or $D_{1B}$ receptor subtype in rodents, and like receptor subtypes. In another embodiment, the partial and/or full $D_1$ dopamine receptor agonist can exhibit activity at both the $D_1$ and $D_2$ dopamine receptor subtypes. For example, the full $D_1$ dopamine receptor agonist can be about equally selective for the $D_1$ and $D_2$ dopamine receptor subtypes, or can be more active at the $D_1$ compared to the $D_2$ dopamine receptor subtypes. In another embodiment, the partial and/or full $D_1$ dopamine receptor agonist can be selective for a $D_1$ dopamine receptor or receptor subtype associated with a particular tissue. In another embodiment, the partial and/or full $D_1$ dopamine receptor agonist can be selective for a $D_1$ dopamine receptor or receptor subtype capable of exhibiting functional selectivity with the $D_1$ dopamine receptor agonist.

It is to be further understood that references to receptor selectivity include functional selectivity at dopamine receptors. Such functional selectivity may further distinguish the activity of the compounds and compositions described herein to allow the treatment of more specifically predetermined symptoms. For example, compounds and compositions that are selective for a particular dopamine receptor, illustratively the $D_1$ receptor, may yet exhibit a second layer of selectivity where such compounds and compositions show functional activity at dopamine $D_1$ receptors in one or more tissues, but not in other tissues. Illustrative of such functional selectivity is the reported selectivity of dihydrexidine for postsynaptic neurons over presynaptic neurons. Other functional selectivity is contemplated herein.

For example, dihydrexidine, (±)-trans-10,11-dihydroxy-5,6,6a,7,8,12b-hexahydrobenzo[a]phenanthridine hydrochloride, which is a dopamine $D_1/D_5$ receptor agonist, has been reported to have nanomolar affinity and about 12-fold to about 60-fold selectivity for the $D_1$ over the $D_2$ receptor (2.2 nM and 183 nM, respectively). Phamacokinetic studies in rodents and non-human primates have shown that significant blood levels can be measured following intravenous (iv), subcutaneous (sc), and oral (po) administration. These studies also show that this drug is cleared rapidly from plasma. However, the pharmacodynamic studies demonstrate a much longer duration of action exhibited with the sc route of administration, than might be expected from the plasma half-life of dihydrexidine.

The compounds, compositions, and methods described herein may be evaluated by using conventional animal models for cognition, such as for routine optimization of dosages, dosage forms, and the like. Illustratively, animal models include evaluation of reference memory in a radial arm maze (Packard et al., J. Neurosci. 9:1465-72 (1989)); Packard and White, Behay. Neural. Biol. 53:39-50 (1990)); Colombo et al., Behay. Neurosci. 103:1242-1250 (1989)), active (Kirby & Polgar, Physiol. Psychol. 2:301-306 (1974)) and passive avoidance (Packard & White, Behay. Neurosci. 105: 295-306 (1991)); Polgar et al., Physiol. Psychol. 9:354-58 (1981)), delayed response performance (Arnsten et al., Psychopharmacol. 116:143-51 (1994)), Morris water maze (Wishaw et al., Behay. Brain Res. 24:125-138 (1987)) and split-T maze (Colombo et al. (1989)). It is appreciated that lesions of the nigrostriatal tract with 6-hydroxydopamine (6-OHDA) impair a variety of learning tasks including avoidance conditioning (Neill et al., Pharmacol. Biochem. Behay. 2:97-103 (1974)) and Morris water maze (Wishaw & Dunnett, Behay. Brain. Res. 18:11-29 (1985); Archer et al., Pharmacol. Biochem. Behay. 31:357-64 (1988)), each of which may be used to evaluate the compounds, compositions, and methods described herein. The disclosures of each of the foregoing are incorporated herein by reference.

The compounds described herein may contain one or more chiral centers, or may otherwise be capable of existing as multiple stereoisomers. It is to be understood that in one embodiment, the invention described herein is not limited to any particular sterochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may be include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

In particular, it is appreciated that the octahydrobenzoisoquinoline compounds described herein have asymmetric carbon atoms or chiral centers, and that each of the stereoisomers (e.g., enantiomers and/or diastereomers) may be prepared in or isolated in optically pure form, or in various mixtures of enantiomers or diastereomers. Each of the individual stereochemically pure isomers of the foregoing are contemplated herein. In addition, various mixtures of such stereochemically pure isomers are also contemplated, including but not limited to racemic mixtures that are formed from one pair of enantiomers.

As used herein, the term "alkyl" includes a chain of carbon atoms, which is optionally branched. It is to be further understood that alkyl is advantageously of limited length, including $C_1$-$C_{24}$, $C_1$-$C_{12}$, $C_1$-$C_8$, $C_1$-$C_6$, $C_1$-$C_4$, and $C_1$-$C_2$.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. It is to be further understood that chain forming cycloalkyl is advantageously of limited length, including $C_3$-$C_{24}$, $C_3$-$C_{12}$, $C_3$-$C_8$, $C_3$-$C_6$, and $C_5$-$C_6$.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic groups, including aromatic carbocyclic and aromatic heterocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, acyloxy, and the like, each of which is optionally substituted. The term "hydroxy derivative" also includes carbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, acylcarbonyl, and the like, each of which is optionally substituted.

As used herein, the term "carboxylate and derivatives thereof" includes the group $CO_2H$ and salts thereof, and esters and amides thereof, and CN.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

As used herein, the term "optionally substituted aryl" includes the replacement of hydrogen atoms with other functional groups on the aryl that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

Illustrative substituents include, but are not limited to, a radical $-(CH_2)_x Z^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or $Z^X$ is selected from —$CO_2R^4$ and —$CONR^5R^6$, where $R^4$, $R^5$, and $R^6$ are each independently selected in each occurrence from hydrogen, $C_1$-$C_6$ alkyl, and aryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as OH and $NR_2$. Illustrative prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, ($C_3$-$C_{20}$)alkanoyl; halo-($C_3$-$C_{20}$)alkanoyl; ($C_3$-$C_{20}$)alkenoyl; ($C_4$-$C_7$)cycloalkanoyl; ($C_3$-$C_6$)-cycloalkyl($C_2$-$C_{16}$)alkanoyl; optionally substituted aroyl, such as unsubstituted aroyl or aroyl substituted by 1 to 3 substituents selected from the group consisting of halogen, cyano, trifluoromethanesulphonyloxy, ($C_1$-$C_3$)alkyl and ($C_1$-$C_3$) alkoxy, each of which is optionally further substituted with one or more of 1 to 3 halogen atoms; optionally substituted aryl($C_2$-$C_{16}$)alkanoyl, such as the aryl radical being unsubstituted or substituted by 1 to 3 substituents selected from the group consisting of halogen, ($C_1$-$C_3$)alkyl and ($C_1$-$C_3$) alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, ($C_1$-$C_3$)alkyl, and ($C_1$-$C_3$)alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The term "pharmaceutically acceptable salts" as used herein refers to those salts formed using organic or inorganic acids that are suitable for use in contact with the tissues of humans and lower animals without undue toxicity, irritation, allergic response, and the like. Acids suitable for forming pharmaceutically acceptable salts of biologically active compounds having amine functionality are well known in the art. The salts can be prepared according to conventional methods in situ during the final isolation and purification of the present compounds, or separately by reacting the isolated compounds in free base form with a suitable salt forming acid.

Pharmaceutically acceptable salts are well known in the art, as exemplified, for example, by S. M. Berge et al., who describe pharmaceutically-acceptable salts in detail in J. Pharm. Sci., 66: 1-19, 1977. The salts may be prepared in situ during the final isolation and purification of the compounds of Formula (I), or separately by reacting the free base function with a suitable organic, mineral, sulfonic, or like acid. Representative acid-addition salts include hydrochloride, hydrobromide, sulfate, bisulfate, acetate, oxalate, valerate, oleate, palmitate, stearate, laurate, borate, benzoate, lactate, phosphate, toluenesulfonate, methanesulfonate, citrate, maleate, fumarate, succinate, tartrate, ascorbate, glucoheptonate, lactobionate, lauryl sulfate salts, and the like.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

The term "pharmaceutically acceptable" includes those salts, carriers, diluents, and excipients that are within the scope of sound medical judgment, suitable for use in contact with the tissues of humans and lower animals without undue toxicity, irritation, allergic response and the like, and are commensurate with a reasonable benefit/risk ratio, effective for their intended use in the treatment of psychological, neurological, cardiovascular and addictive behavior disorders.

The term "pharmaceutically acceptable carriers" includes nontoxic, inert solid, semi-solid or liquid filler, diluent, encapsulating material or formulation auxiliary of any type. Illustrative examples of the materials that can serve as pharmaceutically-acceptable carriers are sugars, such as lactose, glucose and sucrose: starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringers solution; ethyl alcohol and phosphate buffer solutions, as well as other non-toxic compatible substances used in pharmaceutical formulations. Wetting agents, emulsifiers and lubricants, such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Illustrative examples of pharmaceutically-acceptable antioxidants include water-soluble antioxidants, such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, alpha-tocopherol and the like; and the metal chelating agents, such as citric acid, ethylenediamine tetraacetic acid (EDTA), sorbitol, tartaric acid, phosphoric acid and the like. In one aspect, the pharmaceutically acceptable carrier, diluent, or excipient are those generally regarded as safe (GRAS).

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill In one embodiment, the dopamine-related dysfunction treatable with the compounds and methods described herein includes the loss of striatal dopamine within the basal ganglia, the region of the mammalian brain that is involved with motor control. Such dopamine deficiency has been established as the fundamental deficit in Parkinson's disease, and primary to the etiology of that disease state and other movement disorders. It is appreciated that dopamine agonists, including $D_1$-selective agonists, and agonists that are selective to postsynaptic receptors may increase striatal dopamine levels and provide treatment for Parkinson's disease.

In another embodiment, the dopamine-related dysfunction treatable with the compounds and methods described herein includes an excess of dopamine in the brain, which has been identified as a cause of schizophrenia, a psychiatric illness involving disturbance of thought processes, hallucinations, and loss of touch with reality. In addition, chronic abuse of stimulants, such as amphetamines, known to enhance dopaminergic activity in the brain, can lead to a paranoid psychosis that is clinically indistinguishable from classic paranoid schizophrenia, further supporting this dopamine theory of schizophrenia. It is appreciated that dopamine antagonists may decrease dopamine levels in the brain and provide treatment schizophrenia and other psychiatric illnesses.

In another embodiment, the dopamine-related dysfunction treatable with the compounds and methods described herein includes excess dopamine in the brain's reward system. It has been reported that animals trained to self-administer cocaine will increase their consumption of this drug after treatment with either a $D_1$ or a $D_2$ dopamine receptor antagonist, presumably in order to maintain the elevated dopamine levels responsible for the cocaine's euphorigenic and reinforcing properties. Similarly, it has been reported that dopamine $D_1$ agonists decrease food intake by rats, presumably by direct action of the drug on neural feeding mechanisms. It is appreciated that this interrelationship between dopamine and the brain's reward system might be useful for the treatment of substance abuse and other addictive behavior disorders, including cocaine addiction, nicotine addiction, and eating disorders by administering the dopaminergic agents described herein.

In another embodiment, the dopamine-related dysfunction treatable with the compounds and methods described herein includes a reduction in the central nervous system of certain biogenic amine neurotransmitters, such as dopamine, noradrenaline and serotonin, which may cause affective disorders, the most common psychiatric disorders in adults, characterized by changes in mood as the primary clinical manifestation. It is appreciated that the dopamine agonists described herein may be useful in treating such affective disorders.

In another embodiment, the dopamine-related dysfunction treatable with the compounds and methods described herein includes cognition and attention disorders. Animal studies support the role of dopamine in attention-related behaviors involving search and exploratory activity, distractibility, response rate, ability to discriminate, and the switching of attention. It is appreciated that the compounds described herein may be useful in treating such cognition and attention disorders.

The term "affective disorder" includes disorders that are characterized by changes in mood as the primary clinical manifestation, for example, depression.

The term "attention deficit disorder" includes pediatric neuropsychiatric disorders characterized by inattention, impulsivity, distractibility and sometimes hyperactivity, which replaces the less formal diagnoses of hyperactivity syndrome, hyperkinetic syndrome, minimal brain dysfunction and specific learning disability. The disorder is prevalent among pre-adolescent children and is reflected in poor school performance and social behavior and has been described in experimental reports of impaired perceptual, cognitive and motor function.

The term "cognitive impairment" includes a deficiency in any of the aspects of the cognitive (information processing) functions of perceiving, thinking and remembering.

The term "dopamine-related cardiovascular disorders" includes conditions which can be reversed or improved by administration of dopamine or a dopaminergic agent, either alone or in combination therapy with other classes of cardiovascular agents. The usefulness of dopaminergic agents in cardiovascular diseases, for example in the treatment of shock and congestive heart failure, is based on the known, but incompletely understood, role of dopamine in the cardiovascular system, especially the effects of dopamine on the heart and the ability of dopamine to produce vasoconstriction while maintaining blood flow through renal and mesenteric beds. Also included are other related, potential uses for dopaminergic agents which include, for example, use in renal failure.

The term "dopamine-related neurological and psychological disorders" includes behavioral disorders, such as psychoses and addictive behavior disorders; affective disorders, such as major depression; and movement disorders, such as Parkinson's Disease, Huntington's Disease and Gilles de la Tourette's syndrome; which have been linked, pharmacologically and/or clinically, to either insufficient or excessive functional dopaminergic activity In the CNS. Also included are miscellaneous indications for which dopaminergic agents have been found to be clinically useful. Examples of such indications include disorders characterized by vomiting, such as uremia, gastroenteritis, carcinomatosis, radiation sickness, and emesis caused by a variety of drugs; intractable hiccough and alcoholic hallucinosis.

The term "substance abuse" includes periodic or regular self-administration of psychoactive substances in the absence of medical indications and despite the presence of persistent or recurrent social, occupational, psychological or physical problems that the person knows are caused by or may be exacerbated by continued use of the substance.

In one embodiment, the total daily dose of the compounds described herein is administered to a patient in single or in divided doses, and may be in amounts, for example, from 0.01 to 50 mg/kg body weight or more, or from 0.1 to 30 mg/kg body weight. In one aspect, single dose compositions may contain such amounts or submultiples thereof to make up the daily dose. In another aspect, treatment regimens described herein include administration to a patient in need of such treatment from about 1 mg to about 1000 mg per day of the compounds in multiple doses or in a single dose.

The compounds described herein can be formulated in conventional drug dosage forms. Preferred doses of the present compounds depend on many factors, including the indication being treated, the route of administration, and the overall condition of the patient. For oral administration, for example, effective doses of the present compounds are expected to range from about 0.1 to about 50 mg/kg, more typically about 0.5 to about 25 mg/kg. Effective parenteral doses can range from about 0.01 to about 15 mg/kg of body weight, more typically from about 0.1 to about 5 mg/kg of body weight. In general, treatment regimens utilizing compounds in accordance with the present invention comprise administration of from about 1 mg to about 500 mg of the compounds per day in multiple doses or in a single dose.

The compounds described herein may be formulated in liquid dosage forms for oral administration, and may include pharmaceutically acceptable emulsions, microemulsions, solutions, suspensions, and syrups and elixirs containing conventional inert diluents, such as water. Such compositions may also comprise adjuvants such as wetting agents, emulsifying and suspending agents, sweetening, and flavoring agents. Injectable preparations of the compounds of the present invention can be formulated utilizing art-recognized procedures by dispersing or dissolving an effective dose of the compound in a parenterally acceptable diluent such as water, or more preferably isotonic sodium chloride solution. The parenteral formulations can be sterilized using conventional microfiltration techniques.

The compounds described herein may be formulated in solid compositions. Solid dosage forms for oral administration may include capsules, tablets, pills, powders, and granules. In such solid dosage forms the active compound may be admixed with at least one inert diluent, such as sucrose, lactose or starch, such dosage forms may also comprise, as is normal practice, additional substances other than inert diluents, e.g., tableting lubricants and other tableting aids, such as magnesium stearate and microcrystalline cellulose, binders and/or disintegrants. In the case of capsules, tablets and pills, the dosage forms may also comprise buffering agents. Tablets and pills may additionally be prepared with enteric coatings and other release-controlling coatings. Optionally powder compositions comprising an active compound of this invention and, for example, a starch or sugar carrier can be filled into gelatin capsules for oral administration. Other dosage forms of the compounds of the present invention can be formulated using art-recognized techniques in forms adapted for the specific mode of administration. Solid dosage forms may additionally be prepared with fillers in soft and hard-filled gelatin capsules using such excipients as lactose or milk sugar, as well as high molecular weight polyethylene glycols and the like.

In another embodiment, parenteral preparations are described. The term "parenteral" includes intravenous, intramuscular, intraperitoneal, intrastemal, subcutaneous, and intraarticular injection and infusion techniques.

In another embodiment, injectable preparations are described. Illustratively, sterile injectable aqueous or oleaginous suspensions may be formulated according to the conventional techniques using suitable dispersing or wetting agents and suspending agents. The sterile injectable preparation may also be a sterile injectable solution, suspension or emulsion in a nontoxic parenterally-acceptable diluent or solvent, for example, as a solution in 1,3-butanediol. Among the acceptable vehicles and solvents that may be employed are water, Ringers solution, U.S.P. and isotonic sodium chloride solution. In addition, sterile, fixed oils are conventionally employed as a solvent or suspending medium. For this purpose, any bland fixed oil may be employed, including synthetic mono- or diglycerides. Also, fatty acids, such as oleic acid, are used in the preparation of injectables.

The injectable formulation may be sterilized, for example, by filtration through a bacteria-retaining filter, or by incorporating sterilizing agents in the form of sterile solid compositions which may be dissolved or dispersed in sterile water or other sterile injectable medium lust prior to use.

In order to prolong the effect of a drug, the absorption of a drug may be slowed from subcutaneous or intramuscular injection. Illustratively, a suspension of the drug in a crystalline or amorphous material which has poor water solubility is injected. The rate of absorption of the drug becomes dependent on the rate of dissolution of the drug which is, in turn, dependent on the physical state of the drug, for example, the crystal size of the drug and its crystalline form. Another approach to delaying absorption of a drug is to administer the drug as a solution or suspension in oil. Injectable depot forms may also be made by forming microcapsule matrices of drugs and biodegradable polymers, such as with polylactide-polyglycolide oligomers and polymers. Depending on the ratio of drug to polymer and the composition of the polymer, the rate of drug release may be controlled by this method. Examples of other biodegradable polymers include poly-orthoesters and polyanhydrides. The depot injectables can also be made by entrapping the drug in liposomes or microemulsions which are compatible with body tissues.

Suppositories for rectal administration of the drug may be prepared by mixing the drug with a suitable non irritating excipient, such as cocoa butter and polyethylene glycol, both of which are solid at ordinary temperature, but liquid at the rectal temperature and will therefore melt in the rectum, releasing the drug.

In the case of capsules, tablets and pills, the dosage forms may also comprise buffering agents. Tablets and pills may additionally be prepared with enteric coatings and other release-controlling coatings.

If desired, the compounds described herein can be incorporated into slow release or targeted-delivery systems, such as polymer matrices, liposomes and microspheres.

The active compounds may also be in micro-encapsulated form with one or more excipients as noted above. The solid dosage forms of tablets, dragees, capsules, pills, and granules may be prepared with coatings and shells, such as enteric coatings and other coatings well-known in the pharmaceutical formulating art. They may optionally contain opacifying agents, and may also be of a composition that they release the active ingredient(s) only, or preferably, in a certain part of the intestinal tract, optionally In a delayed manner. Examples of embedding compositions which can be used include polymeric substances and waxes.

Dosage forms for topical or transdermal administration of a compound of this invention further include ointments, pastes, creams, lotions, gels, powders, solutions, sprays, inhalants or transdermal patches. The active component is admixed under sterile conditions with a pharmaceutically-acceptable carrier and any needed preservatives or buffers, as required. Ophthalmic formulations, ear drops, eye ointments, powders and solutions are also contemplated as being within the scope of this invention. Administration sublingually, from one or more of the above dosage forms, is also contemplated as a suitable mode of administration of the compounds of the invention.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to the compounds of this invention, excipients, such as lactose, talc, silicic acid, aluminum hydroxide, calcium silicates and polyamide powder, or mixtures of these substances. Sprays may additionally contain customary propellants. such as chlorofluorohydrocarbons or environmentally- and pharmaceutically-acceptable substitutes.

It is appreciated that transdermal patches may have the added advantage of providing controlled delivery of a compound to the body. Such dosage forms may be made by dissolving or dispersing the compound in the proper medium. Absorption enhancers may also be used to increase the flux of the compound across the skin. The rate may be controlled by either providing a rate-controlling membrane or by dispersing the compound in a polymer matrix or gel.

The compounds of the present invention may be administered alone or in combination or in concurrent therapy with other agents which affect the dopaminergic system, for example, L-dopa, amantadine, apomorphine or bromocryptine; and with cholinergic agents, for example, benztropine, biperiden, ethopromazine, procyclidine, trihexylphenidyl, and the like. The compounds of the present invention may also be co-administered with agents, for example, enzyme inhibitors, which block their metabolic transformation outside the CNS. The compounds of the present invention may also be co-administered with other antipsychotic agents. The term "antipsychotic agent" includes drugs used extensively in the symptomatic management of all forms of schizophrenia, organic psychosis, the manic phase of manic depressive illness and other acute idiopathic illnesses and occasionally used in depression or in severe anxiety.

In another embodiment, processes for preparing the compounds are described herein. One illustrative process includes the step of contacting a compound of the formula

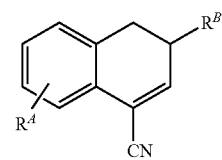

with an anion of 2,4,4-trimethyl-2-oxazolidine to prepare a compound of the formula

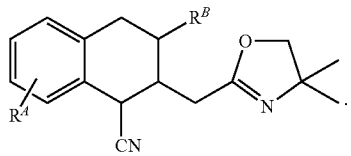

Another illustrative process includes the step of contacting a compound of the formula

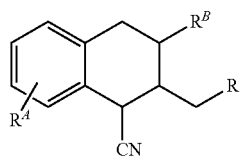

with a reducing agent to prepare a compound of the formula

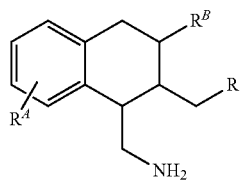

where R is a carboxylic acid or derivative thereof. In one embodiment, the reducing agent includes $CoCl_2$ and $KBH_4$. In another embodiment, R is an oxazoline.

Another illustrative process includes the step of contacting a compound of the formula

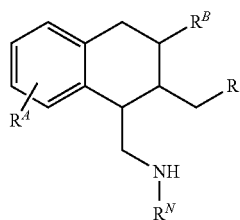

with an acid to prepare a compound of the formula

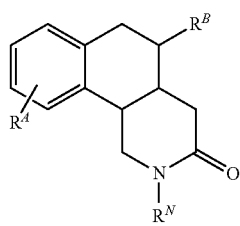

where R is a carboxylic acid or derivative thereof. In one embodiment, acid is included in a protic solvent. In another embodiment, R is an oxazoline. In another embodiment, chiral carbons have the following relative stereochemistry

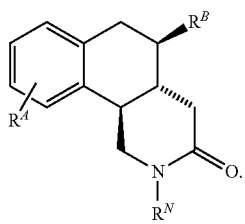

It is appreciated herein that the foregoing processes may be adapted for the preparation of the corresponding optically active compounds.

In another embodiment, the following intermediate compounds useful for the preparation of compounds of Formula (I) are described:

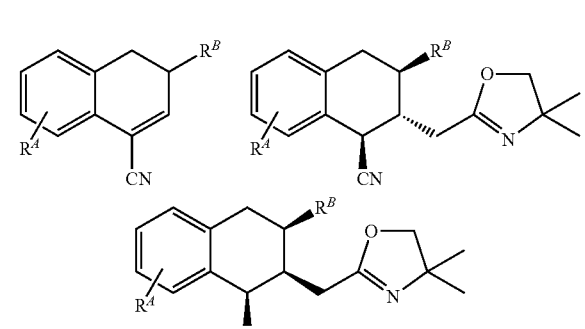

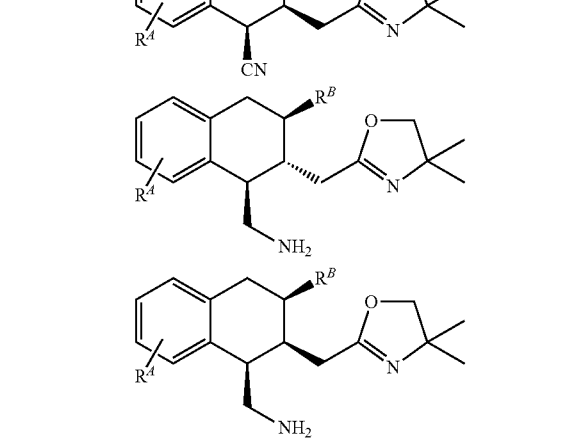

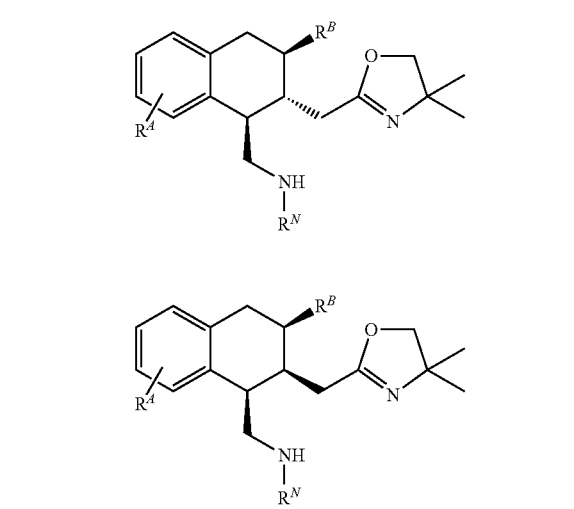

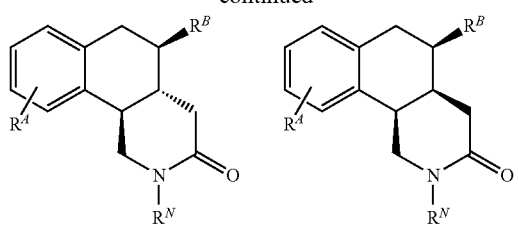

wherein $R^A$, $R^B$, and $R^N$ are as described in the various embodiments herein.

In another embodiment, processes for preparing the compounds are described herein, as follows

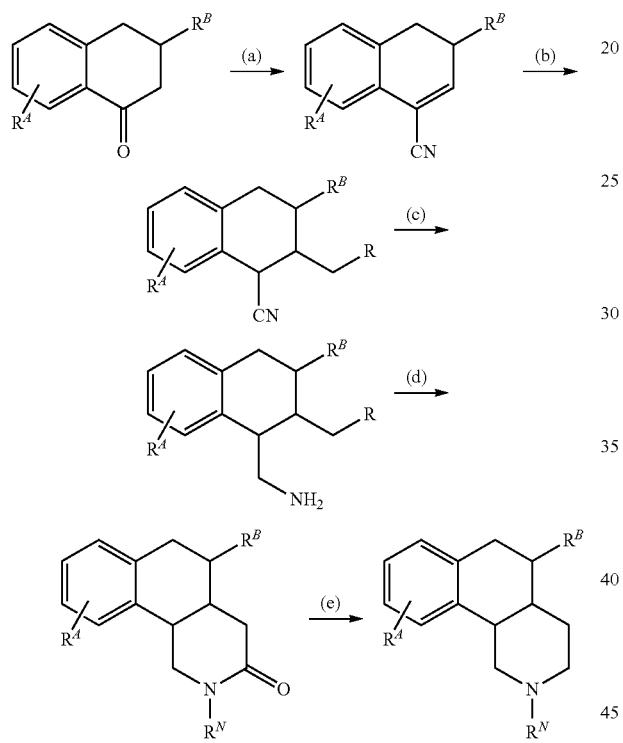

(a) TMSCN, $BF_3Et_2O$, toluene; (b) n-BuLi, 2,4,4-trimethyl-2-oxazoline, THF; (c) $CoCl_2 \cdot 6H_2O$, $KBH_4$ or $NaBH_4$, MeOH; (d) 1. 10% concentrated HCl in EtOH, 2. 6 N NaOH; (e) 1. $BH_3$ THF, 2. 2 N HCl.

wherein $R^A$, $R^B$, and $R^N$ are as described herein; and R is a carboxylic acid or derivative thereof. In another embodiment, R is 4,4-dimethyl-2-oxazolinyl.

In another embodiment, processes for preparing the compounds are described herein, as follows

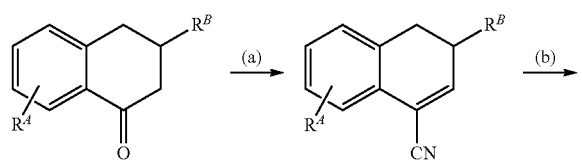

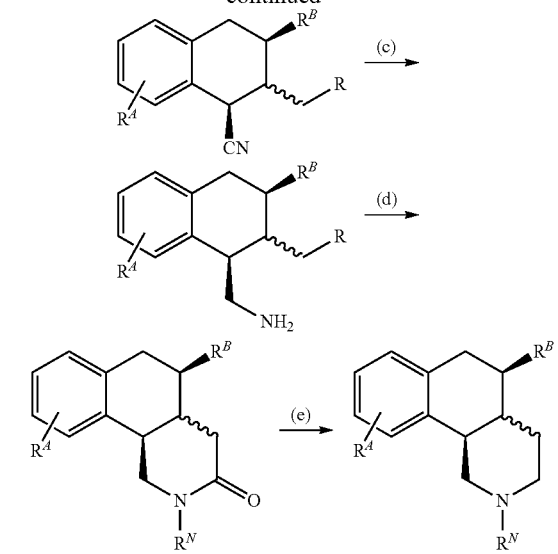

wherein $R^A$, $R^B$, and $R^N$ are as described herein; and R is a carboxylic acid or derivative thereof. In another embodiment, R is 4,4-dimethyl-2-oxazolinyl. It is understood that when $R^B$ is hydrogen, either relative stereochemistry of the group $RCH_2$ added in step (c) may be formed. Alternatively, it is understood that a mixture of compounds may be formed, with varying amounts of the syn and the anti compounds. Alternatively, it is understood that $R^B$ is not hydrogen, the major product formed in step (c) has the anti relative stereochemistry of the group $RCH_2$. The syn and anti compounds may be separated by any conventional technique, such as by chromatography, crystallization, and the like.

Compounds of the following formula

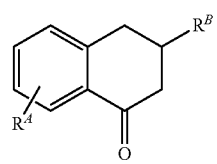

are prepared according to procedures described in U.S. Provisional Patent Application Ser. No. 61/171,273; Schoenleber, R. W., "Dopamine Agonists," W09638435, (1996); Elmore & King, "Synthesis of 8-Isopropylpodocarpane-6,7-Diol (6-Hydroxytotarol) and of 7,8-Dimethoxypodocarpane," J. Chem. Soc., p. 4425 (1961); and Oka et al., "Synthesis of Conformationally Rigid Catecholamine Derivatives," Chem. Pharm. Bull., 25:632-639 (1977), the disclosures of which are incorporated herein by reference.

EXAMPLES

The following illustrative examples describe particular embodiments. However, they are illustrative only, and should not be construed to limit the scope of the specification or the claims.

Example 1

All reagents were commercially available (Aldrich, Alfa Aesar) and were used without further purification unless otherwise indicated. Dry THF was distilled immediately before use from benzophenone-sodium under argon. Column chromatography was carried out using SiliCycle SiliaFlash P60 silica gel (230-400 mesh). J. T. Baker flexible thin layer chromatography sheets (silica gel IB2-F) were used to monitor reaction progress. Melting points were determined using a Mel-Temp apparatus and are reported as uncorrected values. $^1$NMR spectra were recorded using a 300 MHz Bruker ARX300 NMR spectrometer or 500 MHz Bruker DRX500 NMR spectrometer, as noted. Chemical shifts are reported in δ values (ppm) relative to an internal reference (0.03%, v/v) of tetramethylsilane (TMS) in $CDCl_3$, except where noted. Abbreviations used to report NMR peaks are as follows: bs=broad singlet, d=doublet, dd=doublet of doublets, m=multiplet, q=quartet, s=singlet, t=triplet. Chemical ionization mass spectra (CIMS) using isobutane as a carrier gas were obtained with a Finnigan 4000 spectrometer. Elemental analyses were performed by the Purdue University Microanalysis Laboratory or Midwest Microlabs and all compounds reported possess 95% purity or better, unless specifically noted otherwise. All reactions were carried out under an argon atmosphere, unless noted otherwise.

Example 2

2-(2,3-Dimethoxyphenyl)-5-oxo-tetrahydrofuran-3-carboxylic acid (4). Into a flame-dried 3-neck flask, fitted with a condenser and addition funnel were placed 25.0 g (0.184 mol) of anhydrous, powdered $ZnCl_2$. Then 100 mL of $CH_2Cl_2$ were added, followed by 15.3 g (0.092 mol) of 2,3-dimethoxybenzaldehyde and 13.8 g (0.138 mol) succinic anhydride. Triethylamine (25.6 mL, 0.184 mol) was added dropwise to the flask with rapid stirring and the reaction was heated at reflux for 4 days. The reaction was cooled to room temperature and poured over a mixture of ice and conc HCl. The mixture was extracted with EtOAc (3×250 mL), then washed with 2 N HCl (1×250 mL), and brine (1×250 mL). The product was extracted with saturated $NaHCO_3$ (4×200 mL) until TLC indicated no product remaining in the organic layer. The aqueous layer was washed with $CH_2Cl_2$ (1×200 mL) and acidified with conc HCl. The white, milky solution was extracted with $CH_2Cl_2$ (3×250 mL), the organic extracts were dried over $Na_2SO_4$, and evaporated under vacuum to produce 18.0 g (0.068 mol, 73.6%) of pale yellow solid that was recrystallized from EtOAc/hexanes; mp 129-130° C. (lit.[34] mp 132° C.). $^1$H NMR: (300 MHz, $CDCl_3$): δ 7.01 (t, 1H, J=7.5 Hz, ArH); 6.89 (dd, 1H, J=8.1 Hz, J=2.5 Hz, ArH); 6.82 (dd, 1H, J=8.1 Hz, J=2.5 Hz, ArH); 5.73 (d, 1H, J=6.6 Hz, ArCH); 3.81 (s, 3H, $ArOCH_3$); 3.80 (s, 3H, $ArOCH_3$); 3.44 (dt, 1H, J=8.5 Hz, J=6.6 Hz, CHCOOH); 2.90 (d, 2H, J=8.5 Hz, $COCH_2$). EIMS (M$^+$)=266. Additional details are described in Stevens et al., "A New Synthetic Route to Furofuranoid Lignans Via the Intramolecular Mukaiyama Reaction," *J. Chem. Soc., Perkin Trans. 1*, 185-190 (1992), the disclosure of which is incorporated herein by reference.

Example 3

4-(2,3-Dimethoxyphenyl)but-3-enoic acid (5). Recrystallized paraconic acid 4 (8.6 g, 0.032 mol) was placed into a one-neck round bottom flask and the solid was heated in a 180° C. oil bath for 6 h. Carbon dioxide could be observed bubbling out of the dark brown liquid. The reaction was cooled to room temperature and dissolved in $CH_2Cl_2$. The product and any unreacted starting material were extracted into 2 N NaOH (3×100 mL). The pKa of the butenoic acid is approximately 4.2, whereas the pKa of the paraconic acid is approximately 3.6, so the two compounds were separated by titration. The basic aqueous extract was carefully acidified with 2 N HCl, with monitoring by a calibrated pH meter. Once the pH reached 4.5, the solution started becoming slightly cloudy. The solution pH was adjusted to 4.0 and the aqueous solution was extracted with $CH_2Cl_2$. After extraction the pH of the aqueous layer increased to around 5 and the titration was repeated until there was no cloudiness at pH 4.0. The starting material was recovered by acidifying to pH 3.0 and extracting with $CH_2Cl_2$. The initial organic extracts were dried over $Na_2SO_4$, and evaporated under reduced pressure to yield pure 5 that solidified under reduced pressure as a yellow solid (4.7 g, 0.021 mol, 65.2%) that was used without further purification; mp 84-86° C. (no lit.[35] mp reported). $^1$H NMR: (300 MHz, $CDCl_3$): δ 7.08 (dd, 1H, J=1.2, 8.0 Hz, ArH); 6.99 (t, 1H, J=8.0 Hz, ArH); 6.80 (m, 2H, ArH and ArCH=CH); 6.29 (dt, 1H, J=7.2, 15.9 Hz, ArCHCH); 3.84 (s, 3H, $ArOCH_3$); 3.78 (s, 3H, $ArOCH_3$); 3.32 (dd, 2H, J=1.2, 7.2 Hz, $CH_2COOH$). ESIMS (M+Na$^+$)=245.

Example 4

4-(2,3-Dimethoxyphenyl)butanoic acid (6). Acid 5 (3.7 g, 0.017 mol) was dissolved in 25 mL absolute EtOH and added to a Parr hydrogenation bottle containing 0.6 g of 10% Pd/C. The bottle was then pressurized to 25 psi $H_2$ and shaken for 2 h. The contents were then filtered through Celite, the solvents were evaporated, and the resulting oil dried under high vacuum to yield a grey solid (3.7 g, 0.017 mol, quant. yield). The solid was recrystallized from EtOAc/hexanes to produce fine white needles; mp 58-59° C. (lit.[27] mp 58.5-60° C.). $^1$H NMR: (300 MHz, $CDCl_3$): δ 6.97 (t, 1H, J=8 Hz, ArH); 6.76 (d, 1H, J=8 Hz, ArH); 6.75 (d, 1H, J=8 Hz, ArH); 3.84 (s, 3H, $ArOCH_3$); 3.80 (s, 3H, $ArOCH_3$); 2.67 (t, 2H, J=7 Hz, $HO_2CCH_2CH_2$); 2.37 (t, 2H, J=7 Hz, $ArCH_2$); 1.92 (p, 2H, J=7 Hz, $HO_2CCH_2CH_2$). ESIMS (M+Na$^+$)=247.

Example 5

5,6-Dimethoxy-3,4-dihydronaphthalen-1(2H)-one (7). Polyphosphoric acid (15 g) was added to a dry flask with mechanical stirring and heated to 60° C. in an oil bath. Powdered acid 6 (1.0 g, 4.46 mmol) was added in small portions in the center of the stirring vortex. After 30 min the reaction was a rust color and had no remaining starting material. The reaction was quenched by pouring over ice with vigorous stirring and the desired product crystallized. The crystals were collected by filtration to yield pearly off-white plates (900 mg, 4.37 mmol, 97.9%); mp 103-104° C. (lit.[27] mp 104-105° C.). $^1$H NMR: (300 MHz, $CDCl_3$): δ 7.79 (d, 1H, J=8.7, ArH); 6.81 (d, 1H, J=8.7, ArH); 3.86 (s, 3H, $ArOCH_3$); 3.75 (s, 3H, $ArOCH_3$); 2.89 (t, 2H, J=6.3 Hz, $ArCH_2$); 2.53 (t, 2H, J=6.3 Hz, $COCH_2$); 2.05 (p, 2H, J=6.3 Hz, $CH_2CH_2CH_2$). EIMS (M$^+$)=206.

Example 6

5,6-Dimethoxy-3,4-dihydronaphthalene-1-carbonitrile (9). Tetralone 7 (1.7 g, 8.25 mmol) was added as a slurry in freshly distilled toluene (25 mL) to a dried flask with magnetic stirring. TMSCN (1.42 mL, 10.7 mmol) was added dropwise. After stirring for 10 min, $BF_3 \cdot OEt_2$ (1.57 mL, 12.38 mmol) was added with a syringe. The reaction was stirred at room temperature for 3 h, until no starting material remained. The reaction was quenched by pouring over 30 mL ice water and stirring vigorously. To this aqueous mixture were added 20 mL of $Et_2O$, and the layers were separated. The aqueous layer was extracted twice more with Et$_2$O and once with EtOAc. The combined organic layers were dried over Na$_2$SO$_4$, filtered, and evaporated under reduced pressure to afford a tan solid (1.7 g, 7.9 mmol, 96%) that was recrystallized from MeOH to yield fine, colorless needles; mp 138-140° C. (lit.[36] mp 137-139° C.). $^1$H NMR: (300 MHz, CDCl$_3$): δ 7.18 (d, 1H, J=8 Hz, ArH); 6.80 (d, 1H, J=8 Hz, ArH); 6.75 (t, 1H, J=4.6 Hz, ArCH$_2$CH$_2$CH); 3.88 (s, 3H, ArOCH$_3$); 3.76 (s, 3H, ArOCH$_3$); 2.87 (t, 2H, J=8 Hz, ArCH$_2$); 2.44 (m, 2H, ArCH$_2$CH$_2$). EIMS (M$^+$)=215.

Example 7

Cis- and trans-2-((4,4-dimethyl-4,5-dihydrooxazol-2-yl) methyl)-5,6-dimethoxy-1,2,3,4-tetrahydronaphthalene-1-carbonitrile (11a, 11b). To a solution of 2,4,4-trimethyl-2-oxazoline (1.80 mL, 14.2 mmol) in distilled THF (50 mL) in a flask placed on a dry ice/acetone bath were added 7.55 mL (15.1 mmol) of 2.0 M solution of n-BuLi in cyclohexane dropwise with a syringe. The solution slowly turned bright yellow and was stirred at −78° C. for 1 h. Nitrile 9 (2.03 g, 9.44 mmol) was dissolved in distilled THF (50 mL) and added dropwise to the solution of lithiated oxazoline. The yellow color faded and the mixture was stirred at −78° C. for 2 h, followed by 1 h at ambient temperature. The reaction was quenched by the addition of 50 mL of 10% NH$_4$OH in a saturated aqueous NH$_4$Cl. The solution was extracted with Et$_2$O (3×25 mL), and then the organic layers were combined and extracted with 2N HCl (4×25 mL). The aqueous layer was basified with NaHCO$_3$, extracted with Et$_2$O, dried over Na$_2$SO$_4$, filtered, and evaporated. This residue was separated by column chromatography (7:1 EtOAc:hexanes) to give the cis (higher R$_f$, 0.990 g, 3.02 mmol, 31.9%) and trans (lower R$_f$, 1.10 g, 3.35 mmol, 35.5%) addition products. The cis addition product was a colorless oil, but the trans product formed colorless needlelike crystals upon standing; mp 92-94° C. $^1$H NMR: (300 MHz, CDCl$_3$): Cis 11a δ 6.96 (d, 1H, J=8.7 Hz, ArH); 6.77 (d, 1H, J=8.7 Hz, ArH); 4.18 (d, 1H, J=4.5 Hz (cis), ArCHCN); 3.93 (s, 2H, OCH$_2$C(CH$_3$)$_2$); 3.83 (s, 3H, ArOCH$_3$); 3.77 (s, 3H, ArOCH$_3$); 3.00 (ddd, 1H, J=2.4, 5.7, 18.0 Hz, ArCH$_2$); 2.72-2.60 (m, 1H, ArCH$_2$); 2.60-2.52 (dd, 1H, J=8.4, 15.9 Hz, CH$_2$C(N)O); 2.51-2.44 (dd, 1H, J=6.3, 15.9 Hz, CH$_2$C(N)O); 2.46-2.32 (m, 1H, ArCH$_2$CH$_2$); 1.99-1.90 (m, 1H, ArCH$_2$CH$_2$); 1.83-1.68 (m, 1H, ArCH$_2$CH$_2$); 1.28 (s, 3H, C(CH$_3$)$_2$); 1.26 (s, 3H, C(CH$_3$)$_2$). EIMS: (M$^+$)=328. Trans 11b δ 7.11 (d, 1H, J=8.4 Hz, ArH); 6.80 (d, 1H, J=8.4 Hz, ArH); 3.93 (s, 2H, OCH$_2$C (CH$_3$)$_2$); 3.85 (d, 1H, J=9.3 Hz (trans), ArCHCN); 3.83 (s, 3H, ArOCH$_3$); 3.77 (s, 3H, ArOCH$_3$); 2.90 (dt, 1H, J=5.1, 17.7 Hz, ArCH$_2$); 2.75-2.63 (m, 1H, ArCH$_2$); 2.62-2.56 (dd, 1H, J=4.8, 13.5 Hz, CH$_2$C(N)O); 2.50-2.33 (m, 2H, ArCH$_2$CH$_2$, CH$_2$C(N)O); 2.16-2.07 (m, 1H, ArCH(CN)CH); 1.59-1.45 (m, 1H, ArCH$_2$CH$_2$); 1.27 (s, 3H, C(CH$_3$)$_2$); 1.26 (s, 3H, C(CH$_3$)$_2$). EIMS: (M$^+$)=328.

Example 8

Cis-(2-((4,4-dimethyl-4,5-dihydrooxazol-2-yl)methyl)-5, 6-dimethoxy-1,2,3,4-tetrahydronaphthalen-1-yl)methanamine (13a). A solution of cis nitrile 11a (0.880 g, 2.68 mmol) in MeOH (30 mL) was placed in a flask and stirred on an ice bath. Solid CoCl$_2$·6H$_2$O (1.28 g, 5.36 mmol) was added and stirred until all solids dissolved. KBH$_4$ (1.45 g, 0.0268 mol) was then added carefully in three portions over 10 min. The black solution was removed from the ice bath and stirred at ambient temperature for 1 h. The reaction was then quenched by the addition of 10 mL of conc HCl, and the bright blue solution was evaporated to near dryness. The residue was re-dissolved in H$_2$O (50 mL) and washed once with Et$_2$O (10 mL). The aqueous layer was basified with NH$_4$OH and extracted with CH$_2$Cl$_2$ (3×20 mL). The organic layers were combined, dried over Na$_2$SO$_4$, filtered, and evaporated to yield the desired product (0.813 g, 2.45 mmol, 91.2%) as a white solid; mp 208° C. (dec). $^1$H NMR: (300 MHz, CDCl$_3$): δ 6.82 (d, 1H, J=8.4 Hz, ArH); 6.76 (d, 1H, J=8.4 Hz, ArH); 3.84 (s, 3H, ArOCH$_3$); 3.79 (s, 3H, ArOCH$_3$); 3.59 (dd, 1H, J=6.0, 15.6 Hz, CH$_2$NH$_2$); 3.50 (s, 2H, OCH$_2$C(CH$_3$)$_2$); 3.22 (dd, 1H, J=10.8, 15.6 Hz, CH$_2$NH$_2$); 3.04-2.95 (m, 1H, ArCH$_2$); 2.88-2.79 (m, 1H, ArCH); 2.72-2.55 (m, 2H, CH$_2$C(N)O); 2.22-2.13 (m, 1H, ArCH$_2$CH$_2$CH); 2.11-2.01 (m, 1H, ArCH$_2$); 1.77-1.65 (m, 2H, ArCH$_2$CH$_2$); 1.28 (s, 3H, C(CH$_3$)$_2$); 1.26 (s, 3H, C(CH$_3$)$_2$). EIMS (M+)=332.

Example 9

Trans-(2-((4,4-dimethyl-4,5-dihydrooxazol-2-yl)methyl)-5,6-dimethoxy-1,2,3,4-tetrahydronaphthalen-1-yl)methanamine (13b). An identical procedure was used to convert 0.500 g of trans nitrile 11b (1.52 mmol) into the desired amine (0.480 g, 1.45 mmol, 94.1%), recovered as a white solid; mp 181° C. (dec). $^1$H NMR: (300 MHz, CDCl$_3$): δ 6.93 (d, 1H, J=8.4 Hz, ArH); 6.78 (d, 1H, J=8.4 Hz, ArH); 4.18 (dd, 1H, J=5.1, 15.3 Hz, CH$_2$NH$_2$); 3.84 (s, 3H, ArOCH$_3$); 3.80 (s, 3H, ArOCH$_3$); 3.53 (d, 1H, J=17.4 Hz, OCH$_2$C(CH$_3$)$_2$); 3.49 (d, 1H, J=17.4 Hz, OCH$_2$C(CH$_3$)$_2$); 3.22-3.13 (dd, 1H, J=11.1, 15.3 Hz, CH$_2$NH$_2$); 3.08-2.98 (dd, 1H, J=3.9, 17.4 Hz, ArCH$_2$); 2.70-2.56 (m, 1H, ArCH$_2$); 2.54-2.43 (dt, 1H, J=5.1, 11.1 Hz, ArCH); 2.35-2.25 (dd, 1H, J=4.2, 15.9, CH$_2$C(N)O); 2.09-1.98 (dd, 1H, J=12.0, 15.9, CH$_2$C(N)O); 1.94-1.87 (m, 1H, ArCH$_2$CH$_2$); 1.77-1.62 (m, 1H, ArCH$_2$CH$_2$CH); 1.45-1.30 (dq, 1H, J=3.0, 12.6 Hz, ArCH$_2$CH$_2$); 1.27 (s, 3H, C(CH$_3$)$_2$); 1.25 (s, 3H, C(CH$_3$)$_2$). EIMS (M+)=332. Additional details are described in Nichols & Dyer, "Lipophilicity and serotonin agonist activity in a series of 4-substituted mescaline analogues," *J. Med. Chem.*, 20:299-301 (1977), the disclosure of which is incorporated herein by reference.

Example 10

Cis-7,8-dimethoxy-1,2,4,4a,5,6-hexahydrobenzo[h]isoquinolin-3(10bH)-one (15a). Cis amine 13a (0.530 g, 1.60 mmol) was dissolved in 30 mL of 10% H$_2$SO$_4$ in absolute EtOH and the solution was heated at 85° C. for 48 h. The reaction was cooled to room temperature, and 30 mL H$_2$O were added followed by the dropwise addition of 6 N NaOH with stirring until a white solid formed and the reaction pH>12. The basic mixture was stirred for 15 min and the solid was collected by filtration to give the desired lactam as an off-white solid (0.234 g, 0.870 mmol, 54.5%). The filtrate was extracted with EtOAc to recover an additional 0.100 g (0.372 mmol, 23.3%) of the product; mp 185-187° C. $^1$H NMR: (300 MHz, CDCl$_3$): δ 6.83 (d, 1H, J=8.4 Hz, ArH); 6.75 (d, 1H, J=8.4 Hz, ArH); 5.91 (bs, 1H, NH); 3.84 (s, 3H, ArOCH$_3$); 3.80 (s, 3H, ArOCH$_3$); 3.42-3.37 (m, 2H, CH$_2$NH); 3.19-2.99 (m, 2H, ArCH, ArCH$_2$); 2.80-2.63 (m, 2H, ArCH$_2$, COCH$_2$); 2.35-2.29 (d, 1H, J=17.1 Hz, COCH$_2$); 2.32-2.21 (m, 1H, ArCH$_2$CH$_2$CH); 1.90-1.59 (m, 2H, ArCH$_2$CH$_2$). ESIMS (M+H)=262.

Example 11

Trans-7,8-dimethoxy-1,2,4,4a,5,6-hexahydrobenzo[h] isoquinolin-3(10bH)-one (15b). In an identical fashion, 1.24 g (3.73 mmol) of the trans amine 13b was converted into 0.656 g (2.51 mmol, 67.2%) of the trans lactam, a white solid; mp 240° C. (dec). δ 6.86 (d, 1H, J=8.4 Hz, ArH); 6.78 (d, 1H, J=8.4 Hz, ArH); 6.09 (bs, 1H, NH); 3.98-3.91 (dt, 1H, J=4.1, 11.4 Hz, CH$_2$NH); 3.85 (s, 3H, ArOCH$_3$); 3.81 (s, 3H, ArOCH$_3$); 3.18 (t, 1H, J=11.4, CH$_2$NH); 3.13-3.04 (dd, 1H, J=3.9, 17.7 Hz, ArCH$_2$); 2.84-2.72 (dt, 1H, J=5.4, 11.4, ArCH); 2.71-2.59 (m, 1H, ArCH$_2$); 2.64-2.57 (dd, 1H, J=4.8, 17.4, COCH$_2$); 2.24-2.14 (dd, 1H, J=12.3, 17.4, COCH$_2$); 2.03-1.93 (m, 1H, ArCH$_2$CH$_2$); 1.90-1.74 (m, 1H, ArCH$_2$CH$_2$CH); 1.50-1.34 (dq, 1H, J=5.4, 12.4 Hz, ArCH$_2$CH$_2$). ESIMS (M+H)=262.

Example 12

Cis-7,8-dimethoxy-1,2,3,4,4a,5,6,10b-octahydrobenzo[h]isoquinoline HCl (17a). A flame-dried 1-neck flask was charged with 50 mL of distilled THF and 0.130 g (0.498 mmol) of the cis lactam 15a were added. A 1.0 M solution of BH$_3$ in THF (2.49 mL, 2.49 mmol) was added dropwise to the flask and the reaction was heated at reflux overnight. The reaction was then cooled to room temperature, quenched carefully with H$_2$O, and evaporated to about one-third the volume. Following the addition of 10 mL 2N HCl, the solution was stirred at ambient temperature for 4 h. The aqueous solution was washed once with Et$_2$O, basified with NH$_4$OH, and extracted with CH$_2$Cl$_2$ (3×25 mL). The organic layers were combined, dried over Na$_2$SO$_4$, filtered, and evaporated to yield a colorless residue, which was dissolved in Et$_2$O and acidified with 6N HCl in EtOH. The solid that formed was collected by filtration to yield 0.084 g (0.297 mmol, 59.6%) of the isoquinoline HCl 17a as a white powder; mp 186° C. (dec). $^1$H NMR: (500 MHz, DMSO): δ 8.80 (bs, 2H, NH$_2$); 6.87 (m, 2H, ArH); 3.75 (s, 3H, ArOCH$_3$); 3.66 (s, 3H, ArOCH$_3$); 3.18-3.15 (dd, 1H, J=4.2, 12.4 Hz, ArCHCH$_2$NH$_2$); 3.12-3.05 (m, 2H, CH$_2$NH$_2$CH$_2$); 2.99-2.82 (m, 3H, ArCHCH$_2$NH$_2$CH$_2$, ArCH$_2$); 2.59-2.48 (m, 1H, ArCH$_2$); 2.10-1.89 (m, 3H, ArCH$_2$CH$_2$CHCH$_2$); 1.76-1.68 (bd, 1H, J=11.8 Hz, NH$_2$CH$_2$CH$_2$); 1.62-1.54 (m, 1H, ArCH$_2$CH$_2$). ESIMS (M+H)=248.

Example 13

Trans-7,8-dimethoxy-1,2,3,4,4a,5,6,10b-octahydrobenzo[h]isoquinoline HCl (17a). An identical procedure was used to convert 0.500 g (1.92 mmol) of trans lactam 15b into 0.325 g (1.15 mmol, 60.0%) of the trans isoquinoline HCl 17b, a white powder; mp 228° C. (dec). $^1$H NMR: (300 MHz, DMSO): δ 8.91 (bs, 2H, NH$_2$); 6.95 (d, 1H, J=8.7 Hz, ArH); 6.86 (d, 1H, J=8.7 Hz, ArH); 3.96 (d, 1H, J=8.4 Hz, ArCHCH$_2$NH$_2$); 3.76 (s, 3H, ArOCH$_3$); 3.66 (s, 3H, ArOCH$_3$); 3.30 (d, 1H, J=8.4 Hz, ArCHCH$_2$NH$_2$CH$_2$); 2.94-2.81 (m, 2H, ArCHCH$_2$NH$_2$CH$_2$CH$_2$); 2.74-2.55 (m, 3H, ArCH$_2$, ArCHCH$_2$); 1.90-1.79 (m, 2H, ArCH$_2$CH$_2$CHCH$_2$); 1.56-1.30 (m, 3H, ArCH$_2$CH$_2$CH). ESIMS (M+H)=248.

Example 14

Cis-1,2,3,4,4a,5,6,10b-octahydrobenzo[h]isoquinoline-7,8-diol HBr (1). A solution of 17a (0.050 g, 0.177 mmol) in dry CH$_2$Cl$_2$ (15 mL) in a flame-dried single-neck flask was cooled to −78° C., and 0.55 mL of a 1.0 M solution of BBr$_3$ in CH$_2$Cl$_2$ were added dropwise to the flask. The reaction was stirred at −78° C. for 2 h and then at room temperature for 2 h. The reaction was returned to the dry ice/acetone bath and carefully quenched by the addition of 3 mL anhydrous MeOH. The quenched reaction was evaporated to dryness, taking care to keep the water bath below 40° C. The solid residue was redissolved in MeOH, and evaporated again, repeating this process a total of four times. The resulting tan solid was dried under high vacuum overnight and then crystallized from MeOH-Et$_2$O to yield a fine, white powder (0.043 g, 0.144 mmol, 81.1%); mp>250° C. $^1$H NMR: (500 MHz, DMSO): δ 9.08 (s, 1H, ArOH); 8.47 (m, 1H, NH$_2$); 8.34 (m, 1H, NH$_2$); 8.19 (s, 1H, ArOH); 6.60 (d, 1H, J=8.0 Hz, ArH); 6.43 (d, 1H, J=8.0 Hz, ArH); 3.18-3.06 (m, 2H, ArCHCH$_2$NH$_2$CH$_2$); 2.99-2.88 (m, 3H, ArCHCH$_2$NH$_2$CH$_2$); 2.79 (dd, 1H, J=3.5, 17.5 Hz, ArCH$_2$); 2.45-2.33 (m, 1H, ArCH$_2$); 2.04-1.87 (m, 3H, ArCH$_2$CH$_2$CHCH$_2$); 1.71 (bd, 1H, J=16.0 Hz, ArCH$_2$CH$_2$CHCH$_2$); 1.58-1.52 (m, 1H, ArCH$_2$CH$_2$). ESIMS (M+H)=220.

Example 15

Trans-1,2,3,4,4a,5,6,10b-octahydrobenzo[h]isoquinoline-7,8-diol HBr (2). The same procedure was used to convert 0.076 g (0.269 mmol) of trans isoquinoline 17b into 0.056 g (0.187 mmol, 70.0%) of the trans catechol HBr salt 2, crystallized from MeOH-Et$_2$O as a fine, off-white powder; mp>250° C. δ 9.10 (bs, 1H, ArOH); 8.81 (bd, 1H, J=10.5 Hz, NH$_2$); 8.46 (bd, 1H, J=10.5 Hz, NH$_2$); 8.19 (bs, 1H, ArOH); 6.59 (d, 1H, J=8.3 Hz, ArH); 6.49 (d, 1H, J=8.3 Hz, ArH); 3.90 (d, 1H, J=10.5 Hz, ArCHCH$_2$NH$_2$); 3.31 (d, 1H, J=10.5 Hz, ArCHCH$_2$NH$_2$CH$_2$); 3.00-2.81 (m, 1H, ArCHCH$_2$NH$_2$CH$_2$); 2.79-2.73 (dd, 1H, J=5.5, 17.5 Hz, ArCHCH$_2$NH$_2$); 2.70-2.60 (q, 1H, J=11.0 Hz, ArCH$_2$CH$_2$CHCH$_2$); 2.59-2.48 (m, 2H, ArCH$_2$, ArCH); 1.88-1.77 (m, 2H, ArCH$_2$CH$_2$CHCH$_2$); 1.51-1.40 (m, 2H, ArCH$_2$CH$_2$CH); 1.39-1.29 (m, 1H, ArCH$_2$CH$_2$). ESIMS (M+H)=220.

Example 16

5,6-Dimethoxy-3-phenyl-3,4-dihydronaphthalene-1-carbonitrile (10). TMSCN (1.20 mL, 9.22 mmol) was added to a solution of phenyl tetralone 8[30] (2.00 g, 7.09 mmol) in dry toluene (100 mL). BF$_3$.OEt$_2$ (1.34 mL, 10.6 mmol) was then added slowly through a syringe and the reaction was stirred at ambient temperature overnight. The mixture was poured into cold H$_2$O (100 mL) and extracted with EtOAc (3×50 mL). Column chromatography (2:1 EtOAc:hexanes) was used to purify the product and recover 0.674 g (2.39 mmol) of unreacted starting tetralone. The unsaturated nitrile (1.31 g, 4.50 mmol, 63.6%, 95.6% BRSM) was obtained as a white powder; mp 106-107° C. $^1$H NMR: (300 MHz, CDCl$_3$): δ 7.36-7.21 (m, 6H, PhH, ArH); 6.84 (d, 1H, J=8.7 Hz, ArH); 6.78 (d, 1H, J=3.9 Hz, C═CH); 3.90 (s, 3H, ArOCH$_3$); 3.81 (ddd, 1H, J=3.9, 7.2, 11.4 Hz, ArCH$_2$CH); 3.71 (s, 3H, ArOCH$_3$); 3.35 (dd, 1H, J=7.2, 16.5 Hz, ArCH$_2$); 2.92 (dd, 1H, J=11.4, 16.5 Hz, ArCH$_2$). EIMS: (M$^+$)=291.

Example 17

Trans-2-((4,4-dimethyl-4,5-dihydrooxazol-2-yl)methyl)-5,6-dimethoxy-3-phenyl-1,2,3,4-tetrahydronaphthalene-1-carbonitrile (12). In a method analogous to the synthesis of 11 above, nitrile 10 (0.770 g, 2.65 mmol) was converted to the title compound. The trans isomer was crystallized from the crude mixture using 1:1 EtOAc:hexanes to yield 0.262 g (0.649 mmol, 24.5%) of a white powder. The mother liquor was further purified by column chromatography (1:1 EtOAc: hexanes) to isolate 0.378 g (0.936 mmol) of a mixture of the cis and trans isomers of the desired product, from which an additional 0.029 g (0.0718 mmol, 2.7%) of the trans isomer was crystallized; mp 131-133° C. $^1$H NMR: (300 MHz, CDCl$_3$): δ 7.39-7.19 (m, 6H, PhH, ArH); 6.88 (d, 1H, J=8.7 Hz, ArH); 4.57 (d, 1H, J=10.5 Hz (trans), ArCHCN); 3.87 (s, 3H, ArOCH$_3$); 3.88-3.75 (m, 2H, OCH$_2$C(CH$_3$)$_2$); 3.74 (s, 3H, ArOCH$_3$); 3.22 (dd, 1H, J=4.5, 16.8 Hz, ArCH$_2$); 3.03 (dt, 1H, J=4.5, 11.4 Hz, ArCH$_2$CH); 2.81 (dd, 1H, J=11.4, 16.8 Hz, ArCH$_2$); 2.72-2.61 (m, 1H, ArCH(CN)CH); 2.55 (dd, 1H, J=3.9, 16.2 Hz, CH$_2$C(N)O); 2.55 (dd, 1H, J=6.3, 16.2 Hz, CH$_2$C(N)O); 1.27 (s, 3H, C(CH$_3$)$_2$); 1.22 (s, 3H, C(CH$_3$)$_2$). EIMS; (M$^+$)=404.

Example 18

Trans-(2-((4,4-dimethyl-4,5-dihydrooxazol-2-yl)methyl)-5,6-dimethoxy-3-phenyl-1,2,3,4-tetrahydronaphthalen-1-yl) methanamine (14). Analogous to the synthesis of 13, nitrile 12 (0.157 g, 0.389 mmol) was converted to the title compound (0.149 g, 0.365 mmol, 93.7%) as a white solid; mp 213° C. (dec). $^1$H NMR: (300 MHz, CDCl$_3$): δ 7.40-7.22 (m, 5H, PhH); 7.01 (d, 1H, J=8.7 Hz, ArH); 6.83 (d, 1H, J=8.7 Hz, ArH); 4.25 (dd, 1H, J=5.4, 15.0 Hz, ArCHCH$_2$NH$_2$); 3.86 (s, 3H, ArOCH$_3$); 3.77 (s, 3H, ArOCH$_3$); 3.73 (bs, 2H, NH$_2$); 3.51-3.42 (m, 2H, OCH$_2$C(CH$_3$)$_2$); 3.30-3.21 (m, 2H, ArCH$_2$, ArCHCH$_2$NH$_2$); 2.85-2.46 (m, 3H, ArCHCH$_2$NH$_2$, ArCH$_2$CH); 2.01 (dq, 1H, J=5.4, 11.1 Hz, ArCH$_2$CH(Ph)CH); 1.89-1.74 (m, 2H, CH$_2$C(N)O); 1.20 (s, 3H, C(CH$_3$)$_2$); 1.16 (s, 3H, C(CH$_3$)$_2$). ESIMS (M+H)=409.

Example 19

7,8-Dimethoxy-5-phenyl-1,2,4,4a,5,6-hexahydrobenzo[h]isoquinolin-3(10bH)-one (16). As in the synthesis of 15 above, amine 14 (0.200 g, 0.490 mmol) was converted into the desired lactam as a white solid (0.110 g, 0.326 mmol, 66.7%). The filtrate was extracted with EtOAc to recover an additional 0.032 g (0.0950 mmol, 19.4%) of the product; mp>250° C. $^1$H NMR: (300 MHz, CDCl$_3$): δ 7.38-7.19 (m, 5H, PhH); 6.93 (d, 1H, J=8.7 Hz, ArH); 6.82 (d, 1H, J=8.7 Hz, ArH); 5.98 (bs, 1H, NH); 4.00 (dt, 1H, J=4.6, 11.4 Hz, CH$_2$NH); 3.86 (s, 3H, ArOCH$_3$); 3.78 (s, 3H, ArOCH$_3$); 3.37-3.21 (m, 2H, CH$_2$NHCOCH$_2$); 3.20 (dt, 1H, J=5.1, 10.5 Hz, ArCHCH$_2$); 2.83 (dd, 1H, J=12.3, 17.4 Hz, NHCOCH$_2$); 2.66 (dt, 1H, J=4.2, 10.5 Hz, ArCH$_2$CH(Ph)CH); 2.23 (dd, 1H, J=4.2, 17.1 Hz, ArCH$_2$); 2.17-2.04 (m, 1H, ArCH$_2$CH); 1.94 (dd, 1H, J=12.6, 17.1 Hz, ArCH$_2$). ESIMS (M+H)=338.

Example 20

7,8-Dimethoxy-5-phenyl-1,2,3,4,4a,5,6,10b-octahydrobenzo[h]isoquinoline HCl (18). Analogous to the procedure for 17, lactam 16 (0.190 g, 0.564 mmol) was converted into the title compound (0.169 g, 0.471 mmol, 83.7%) as a white powder; mp>250° C. $^1$H NMR: (500 MHz, DMSO): δ 9.15 (bs, 1H, NH$_2$); 8.88 (bs, 1H, NH$_2$); 7.39-7.20 (m, 5H, PhH); 7.04 (d, 1H, J=9.0 Hz, ArH); 6.92 (d, 1H, J=9.0 Hz, ArH); 4.04 (bd, 1H, J=11.0 Hz, CHCH$_2$NH); 3.78 (s, 3H, ArOCH$_3$); 3.64 (s, 3H, ArOCH$_3$); 3.21 (bd, 1H, J=11.5 Hz, CH$_2$CH$_2$NH); 3.03 (d, 1H, J=12.5 Hz, ArCH$_2$); 2.90 (bt, 1H, J=11.0 Hz, ArCH); 2.85-2.68 (m, 4H, ArCH$_2$CH, CH$_2$NH$_2$CH$_2$); 1.91-1.83 (m, 1H, ArCH$_2$CH(Ph)CH); 1.39-1.31 (m, 1H, CH$_2$NH$_2$CH$_2$CH$_2$); 1.29-1.19 (m, 1H, CH$_2$NH$_2$CH$_2$CH$_2$). ESIMS (M+H)=324.

Example 21

5-Phenyl-1,2,3,4,4a,5,6,10b-octahydrobenzo[h]isoquinoline-7,8-diol HBr (3). In a procedure analogous to that for 1, isoquinoline 18 (0.070 g, 0.195 mmol) was converted into the title compound, recrystallized from MeOH-Et$_2$O and isolated as a fine, white powder. (0.044 g, 0.117 mmol, 60.3%); mp>250° C. $^1$H NMR: (300 MHz, DMSO): δ 9.14 (s, 1H, ArOH); 8.81-8.72 (m, 1H, NH$_2$); 8.50-8.35 (m, 1H, NH$_2$); 8.26 (s, 1H, ArOH); 7.38-7.20 (m, 5H, PhH); 6.64 (d, 1H, J=8.4 Hz, ArH); 6.58 (d, 1H, J=8.4 Hz, ArH); 3.97 (bd, 1H, J=9.6 Hz, CHCH$_2$NH); 3.22 (bd, 1H, J=10.8 Hz, CH$_2$CH$_2$NH); 2.95 (d, 1H, J=11.7 Hz, ArCH$_2$); 2.89-2.55 (m, 5H, ArCH$_2$CH, ArCHCH$_2$NH$_2$CH$_2$); 1.91-1.80 (m, 1H, ArCH$_2$CH(Ph)CH); 1.40-1.32 (bd, 1H, J=12.6 Hz, CH$_2$NH$_2$CH$_2$CH$_2$); 1.28-1.12 (m, 1H, CH$_2$NH$_2$CH$_2$CH$_2$). ESIMS (M+H)=296.

Method Example 1

Chemicals and reagents. [$^3$H]-SCH-23390 (81 Ci/mmol) are purchased from Amersham Biosciences (Piscataway, N.J., USA). [$^3$H]-Cyclic AMP (30 Ci/mmol) is purchased from PerkinElmer (Boston, Mass., USA). Dopamine, SCH-23390, butaclamol, isobutyl-methylxanthine, forskolin and most other reagents are purchased from Sigma-Aldrich Chemical Company (St. Louis, Mo., USA). Most cell culture reagents including growth media and antibiotics are purchased from Gibco Invitrogen Corporation (Carlsbad, Calif., USA).

Method Example 2

Production of Cell Lines. Lipofectamine 2000 is used according to manufacturers instructions to transfect HEK293 cells with the gene encoding the human D$_1$ (hD$_1$) receptor in the pcDNA3.1/V5-His-TOPO vector. G418 (600 μg) is used to select stably expressing cells. After four weeks in selection media, the cells are split to create pooled cell lines that are individually assayed for D$_1$ receptor expression and function by measuring [$^3$H]-SCH-23390 binding and cAMP accumulation.

Method Example 3

Cell Culture. All cells are maintained in DMEM with 5% fetal clone serum, 5% bovine calf serum, 0.05 μg/mL penicillin, 50 μg/mL streptomycin, and 300 μg G418. Cells are grown at 37° C. in a humidified incubator with 6% CO$_2$.

Method Example 4

Cyclic AMP Accumulation Assay. Assays are performed on confluent monolayers of cells in 96-well plates. All drugs are diluted in Earle's balanced salt solution (EBSS) assay buffer (EBSS containing 2% bovine calf serum, 0.025% ascorbic acid, and 15 mM HEPES, pH 7.4) and added in triplicate on ice. Cyclic AMP stimulation assays are performed in HEK hD$_1$ cells by incubating with agonists for 15 minutes at 37° C. All assays are performed in the presence of 500 μM isobutyl-methylxanthine (IBMX) and terminated with 3% trichloroacetic acid.

Method Example 5

Cyclic AMP Binding Assay. Accumulation assays are quantified using a previously described protocol: Cellular lysate is added to cAMP binding buffer (100 mM Tris-HCl, pH 7.4, 100 mM NaCl, 5 mM EDTA) in assay tubes containing [$^3$H]-cyclic AMP (1 nM final concentration) and bovine adrenal gland cAMP binding protein (100-150 μg in 500 μl buffer). These are incubated at 4° C. on ice for 2-3 hours and terminated by harvesting with ice cold wash buffer (10 mM Tris, 0.9% NaCl) using a 96-well Packard Filtermate cell harvester. 30 μl of Packard Microscint O is added to each well after drying. Radioactivity is counted using a Packard Topcount scintillation counter. Standard curves ranging from 0.01 to 300 pmol of cAMP are used to determine the concentration of cAMP in each sample.

Method Example 6

Competitive Binding Experiments. Porcine striatal tissue is obtained from the Purdue Butcher Block and prepared as described in the literature. Striatal tissue is homogenized using a potter-type homogenizer, suspended in homogenization buffer (20 mM Hepes, 0.32 M sucrose, pH 7.4), and spun at 1,000 g for 10 minutes at 4° C. The pellet (P1) is discarded and supernatant is centrifuged at 30,000 g for 10 minutes at 4° C. The resultant pellet (P2) is resuspended in 50 mM Tris buffer (pH 7.4) by briefly using a Kinematica homogenizer, and then centrifuged at 30,000 g for 30 minutes at 4° C. This pellet is resuspended again in 50 mM Tris buffer, dispensed into 1 mL aliquots, and centrifuged for 10 min. at 13,000 g at 4° C. A BSA protein assay is used to determine the final weight of the pellets. Supernatant is aspirated and pellets are frozen at −80° C. until use.

Receptor and competitive binding experiments are performed as described in the literature. Pellets are resuspended (1 mL/mg) in receptor binding buffer (50 mM Hepes, 4 mM $MgCl_2$, pH 7.4) and 75 μg protein is used per well. Receptor isotherms are performed with $[^3H]$-SCH-23390 and $[^3H]$-spiperone to determine $B_{max}$ and $K_d$ for $D_1$-like and $D_2$-like receptor sites, respectively (760 fmol/mg and 0.44 nM for $[^3H]$-SCH-23390, 250 fmol/mg and 0.075 nM for $[^3H]$-spiperone). All $D_2$-like receptor binding assays are performed in the presence of 50 nM ketanserine to mask $5$-$HT_{2A}$ sites. Nonspecific binding is defined by 5 μM butaclamol. Drug dilutions for competitive binding experiments are made in receptor binding buffer and added to wells containing either 1 nM $[^3H]$-SCH-23390 or 0.15 nM $[^3H]$-spiperone and 75 μg protein. All binding experiments are incubated for 30 minutes at 37° C., and are terminated and counted in a similar fashion to the cAMP binding assays.

The receptor binding affinities ($K_i$, nM) for porcine striatal binding of illustrative compounds described herein are shown in the following table (DOX refers to Example 24 of U.S. patent application Ser. No. 12/195,141).

| Compound | D1-like | D2-like | D1 Selectivity |
|---|---|---|---|
| 1 | 6800 ± 490 | 2800 ± 210 | 0.4 |
| 2 | 850 ± 65 | 670 ± 36 | 0.8 |
| 3 | 6 ± 0.2 | 440 ± 72 | 73 |
| SCH-23390 | 0.79 ± 0.10 | ND | NA |
| Chlorpromazine | ND | 3.2 ± 0.50 | |
| DOX | 18 ± 0.6 | 4400 ± 620 | 240 |

Method Example 7

Data Analysis. GraphPad Prism software is used to generate dose-response, receptor isotherm, and competition binding curves and to perform statistical analyses (GraphPad Software, San Diego, Calif.). For functional experiments, Hill slopes are fixed at 1. For competitive binding analysis, when data points do not reach complete competition with the radioligand, bottoms of curves are normalized to non-specific values. $K_i$ values are calculated from $IC_{50}$ using the Cheng-Prusoff equation.

Method Example 8

MPTP-Treated Monkeys as a Model for Parkinson's Disease Subjects and Behavioral Testing. Two adult male Macaca fascicularis monkeys (4.7 and 5.7 kg initial body weight) and 1 female Macaca nemistrina monkey (5.0 kg initial body weight) are trained to perform a delayed response task. Briefly, animals are trained and tested on delayed response while seated in a restraining chair placed inside a sound attenuating modified Wisconsin General Test Apparatus. The monkeys sit behind an opaque screen that when raised, allows access to a sliding tray that contains recessed food wells with identical sliding white Plexiglas covers that serve as stimulus plaques that can be displaced by the animal to obtain rewards (e.g. raisins). Monkeys are trained to retrieve a raisin from one of the food wells after observing the experimenter bait the well. Right and left wells are baited in a randomized, balanced order. Animals are maintained on a restricted diet during the week and tested while food deprived.

Training is accomplished with a non-correction procedure, beginning with a 0 s delay and progressing to a 5 s delay. Animals are trained until performance with a 5 s delay is 90% correct or better for at least 5 consecutive days. Each daily session consists of 25 trials. A response is scored a "mistake" if the monkey makes its response choice to a well that is not baited with reward. A "no response" error is scored if the monkey fails to respond to a trial within 30 s.

Toxin Administration. Once animals are performing at criterion level, MPTP administration begins. MPTP-HCl (in sterile saline) is administered intravenously two or three times per week while animals are seated in the restraining chair with an ankle cuff limiting movement of one leg. The monkeys are trained to allow the experimenter to hold one leg and to not struggle during intravenous injection into the saphenous vein. Personnel administering MPTP wear a disposable gown, latex gloves, and a face mask with a splash shield. Following administration of the toxin, the used syringe is filled with a saturated solution of potassium permanganate (to oxidize any remaining MPTP), capped, and discarded as hazardous waste. Waste pans located beneath the animals' cages and any excreta located in those pans are sprayed with a potassium permanganate solution prior to disposal of the excreta. Laboratory animal care personnel take care not to generate aerosols during cage cleaning.

MPTP is administered to each animal in doses ranging from 0.05 mg/kg at the start of the study to 0.20 mg/kg. Animals receive cumulative MPTP doses of 64.7 mg, 23.9 mg, and 61.7 mg on a variable dosing schedule over periods of 346 days, 188 days, and 341 days, respectively. The different total amounts of MPTP administered reflect variability in individual animal sensitivity and response to the toxin. Although animals receive different total amounts of toxin over different time periods, the nature of the cognitive deficits are similar in all animals.

Drug Administration. Pharmacological data are obtained after animals consistently showed at least a 15% performance deficit on delayed response. Compounds and/or compositions described herein are tested by dissolving in physiological saline containing 0.2% ascorbate and administering subcutaneously. Illustratively, compounds and/or compositions described herein are used at 0.3, 0.6, and 0.9 mg/kg doses, calculated as the free base where appropriate. The order of dose administration is determined randomly. Each dose is tested at least twice in each animal. On some trials, compounds and/or compositions described herein are administered in combination with the dopamine $D_1$ receptor antagonist, such as SCH-23390 (0.0075 or 0.015 mg/kg). On such trials, SCH-23390 is administered 15 min prior to the compounds and/or compositions described herein.

Delayed response testing begins 8 min after administration of compounds and/or compositions. On drug testing days, animals are tested for delayed response performance, administered compounds and/or compositions (or saline), and re-tested on the delayed response task. Saline control trials are performed approximately once every third test session. Saline injections control for effects of receiving an injection and for possible changes in performance as a consequence of being tested a second time in one day. A minimum of 3 days separate compounds and/or compositions trials in any particular animal. Compounds and/or compositions test sessions are conducted only if subjects meet the 15% or more performance deficit requirement on any particular day.

Data Analysis. Delayed response performance after compound and/or composition administration is compared with matched control performance obtained on the same day prior to drug administration. The total number of correct responses as well as the number of mistakes and "no response" errors are tabulated for each test session. Data are then expressed as mean (±standard deviation) performance. All animals serve as their own controls and statistical analyses consist of analysis of variance, repeated measures design, with post hoc comparisons (Bonferroni t test).

Method Example 9

Unilateral 6-OHDA Lesion Model for Parkinson's Disease. Summary. In the rat unilateral 6-hydroxydopamine (6-OHDA) rotation model of Parkinson's disease, 6-OHDA is infused unilaterally into the medial forebrain bundle, the substantia nigra, or the striatum. This treatment results in the destruction of dopamine terminals and neurons and a loss of striatal dopamine, and a profound functional dopaminergic supersensitivity develops on the lesioned side. When challenged with direct-acting dopamine receptor agonists, unilateral 6-OHDA rats turn contralaterally (away from the side of the lesion) because of the increased sensitivity of the postsynaptic dopamine receptors on the lesioned side. The experiments described below examine tolerance induced by the compound and/or composition using the 6-OHDA model.

Subjects. Adult male Sprague-Dawley Rats (Hilltop Laboratories, Chatsworth, Calif.), weighing between 280 and 320 grams, are used as subjects. Animals are housed individually with food and water available ad libitum, except as noted below. The light:dark schedule is 12 h:12 h, and testing is performed during the light cycle. All methods adhere to the guidelines in the Guide for the Care and Use of Experimental Animals published by the National Institutes of Health (Pub. 85-23, 1985).

Surgery. Rats are pretreated with 25 mg/kg desipramine (s.c.) approximately 30 minutes before surgery. Rats are anesthetized by inhalation of isoflurane (1.5 to 4.0%) and placed in a stereotaxic apparatus. An infusion cannula is placed in the medial forebrain bundle at the coordinates A.P. −3.8 mm, M.L. −1.5 mm, and D.V. −3.8 mm relative to bregma according to the atlas of Paxinos and Watson (1986). Ten micrograms of 6-OHDA (6-hydroxydopamine; Sigma Chemical Co., St. Louis, Mo.) in a volume of 4 μL is infused at a rate of 0.5 μL/min in a vehicle of 0.01% ascorbate. After a 14-day recovery period, rats are prescreened for rotation in response to d-amphetamine (5 mg/kg) and to apomorphine (0.3 mg/kg) 1 week later. Animals that respond to both d-amphetamine (>800 rotations in 3 h) and apomorphine (>100 rotations in 1 h) are retained for further study.

Testing of compounds begins on day 28 postsurgery in each case. A new group of 6-OHDA-lesioned rats is used for each new study. In some studies, rats are implanted with a subcutaneous 14-day osmotic minipump (model 2 ML2, Alza, Palo Alto, Calif.) with a flow rate of 5.0 μL/h. The rats are re-anesthetized with 1.5 to 4% isoflurane, a small incision is made on the back of the neck, and the minipump is placed subcutaneously in the cavity. The incision is closed with sterile wound clips. Before implantation, minipumps are incubated in sterile saline (37° C.) to ensure outflow at the time of implantation. The minipumps are used to administer dinapsoline, or vehicle (50% dimethyl sulfoxide (DMSO), 12.5% ascorbic acid).

Striatal Dopamine Content. In a subset of animals, striatal dopamine content is measured to confirm the extent of the 6-OHDA lesion. At the completion of the study, animals are anesthetized deeply by $CO_2$ inhalation and rapidly decapitated using a guillotine. Brains are removed quickly, and kept on ice while right and left striata are isolated, removed, and weighed in individual nonfilter micro-centrifuge tubes containing 0.5 mL of a homogenizing buffer (0.22 N perchloric acid, 0.5% EDTA, 0.15% sodium metabisulfite). The samples are homogenized by sonication for 10 seconds and then centrifuged at 14,000 g for 20 minutes. The supernatant is transferred to microcentrifuge tubes with a filter (0.2 μm) and centrifuged at 14,000 g for 2 minutes. The samples are frozen at −80° C. to await HPLC analysis.

HPLC Analysis. Thawed samples are analyzed for dopamine content using established high performance liquid chromatography (HPLC)-electrochemical detection methods. Briefly, 50 μL samples are injected into the sample loop of an HPLC system using an acetate buffer mobile phase (17% methanol) pumped at 0.4 mL/min. Peaks are separated with a C-18 reverse phase column (3 mm diameter, MD-180, ESA, Chelmsford, Mass.) and detected with a dual coulometric cell (5014B, ESA) and detector (Coulochem II, ESA). Dopamine is analyzed by sequential reduction (−100 mV) and oxidation (350 mV) and is quantified at the latter electrode. Dopamine concentration in each sample is calculated in reference to established standard curves and is represented as picomoles per milligram of striatal tissue. Depletion is calculated as the percentage of dopamine content on the lesioned side relative to the nonlesioned side.

Apparatus, Procedure, and Statistics. Rats are tested for rotation in automated rotation chambers (Rotoscan, Accuscan, Columbus, Ohio). The apparatus consists of a cylindrical Plexiglas chamber 30 cm in diameter in which the animal is fitted to a harness attached to a flexible rod connected to a rotating microswitch. Animals are allowed to habituate to chambers for 30 minutes before drug treatment in each case. Data are collected for 1 to 12 h after injection, using 15 minute time bins. Treatments are compared using one-way and repeated measures of analysis of variance (ANOVA), as appropriate; post hoc analysis is performed with Dunnett's test.

Acute Compound and/or Composition Administration. Beginning 1 week after the screening dose with apomorphine, subjects (n=12) are tested once per week with compound and/or composition (0.02, 0.2, or 2 mg/kg) or vehicle (s.c.) using a counterbalanced design, and rotation behavior is monitored for 10 h. After the final day of testing, rats are euthanized and brains are removed for subsequent assessment of dopamine depletion. In the oral dosing experiments, a separate group of subjects (n=8) receive compound and/or composition (0.02, 0.2, or 2 mg/kg) or vehicle once per week using a counterbalanced design. Rats are fasted for 16 h before dosing with oral gavage, and rotation behavior is monitored for 10 h.

In the experiments that include acute antagonist administration, subjects (n=8/group) are pretreated with either the $D_1$ antagonist SCH-23390 (0.5 mg/kg s.c.), the $D_1$ antagonist raclopride (2 mg/kg s.c.), or vehicle. After 30 minutes, they are injected with compound and/or composition (0.2 or 2 mg/kg s.c.), and rotation is monitored for 3 h. The shortened assessment period is chosen, because the $D_1$ antagonist SCH-23390 is known to have a relatively short duration of action (approximately 3 h) in the assay.

What is claimed is:

1. A compound of the formula

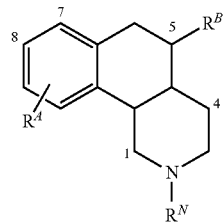

or a pharmaceutically acceptable salt thereof, wherein:
$R^A$ is 7,8-dihydroxy;
$R^B$ is phenyl, optionally substituted with substituents selected from the group consisting of hydroxy, amino, and carboxylic acid; and
$R^N$ is hydrogen; and
wherein the chiral carbons have the following relative stereochemistry

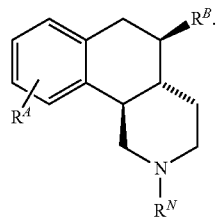

2. A pharmaceutical composition comprising one or more compounds of claim 1, and one or more pharmaceutically acceptable carriers, excipients, or diluents therefor.

3. The compound of claim 1, wherein said compound is 5-phenyl-1,2,3,4,4a,5,6,10b-octahydrobenzo[h]isoquinoline-7,8-diol, or a pharmaceutically acceptable salt thereof.

4. The compound of claim 3, wherein said pharmaceutically acceptable salt is a HBr salt.

* * * * *